United States Patent
Fang et al.

(10) Patent No.: US 10,160,768 B2
(45) Date of Patent: Dec. 25, 2018

(54) STEREOCHEMICALLY DEFINED POLYPROPIONATES AND METHODS FOR MAKING AND USING THE SAME

(71) Applicant: Eisai R&D Management Co., Ltd., Tokyo (JP)

(72) Inventors: Francis G. Fang, Andover, MA (US); Hyeong-Wook Choi, Andover, MA (US); Silvio Campagna, Thousand Oaks, CA (US); Steven Mathieu, Windham, NH (US)

(73) Assignee: Eisai R&D Management Co., Ltd., Tokyo (JP)

( * ) Notice: Subject to any disclaimer, the term of this patent is extended or adjusted under 35 U.S.C. 154(b) by 0 days.

(21) Appl. No.: 15/501,658

(22) PCT Filed: Aug. 4, 2015

(86) PCT No.: PCT/US2015/043535
§ 371 (c)(1),
(2) Date: Feb. 3, 2017

(87) PCT Pub. No.: WO2016/022519
PCT Pub. Date: Feb. 11, 2016

(65) Prior Publication Data
US 2017/0240560 A1    Aug. 24, 2017

Related U.S. Application Data

(60) Provisional application No. 62/032,757, filed on Aug. 4, 2014.

(51) Int. Cl.
| | |
|---|---|
| *C07D 493/18* | (2006.01) |
| *C07D 493/22* | (2006.01) |
| *C07B 57/00* | (2006.01) |
| *C07D 313/00* | (2006.01) |
| *C07D 493/08* | (2006.01) |

(52) U.S. Cl.
CPC ............ *C07D 493/22* (2013.01); *C07B 57/00* (2013.01); *C07D 313/00* (2013.01); *C07D 493/08* (2013.01); *C07D 493/18* (2013.01)

(58) Field of Classification Search
CPC .................................................. C07D 493/18
See application file for complete search history.

(56) References Cited

U.S. PATENT DOCUMENTS

| 7,189,715 B2 | 3/2007 | Jerussi et al. |
| 7,700,783 B2 | 4/2010 | Smith, III et al. |
| 2002/0052028 A1 | 5/2002 | Santi et al. |

OTHER PUBLICATIONS

International Search Report (PCT/ISA/210) dated Nov. 2, 2015, by the U.S. Patent Office as the International Searching Authority for International Application No. PCT/US2015/043535.
Written Opinion (PCT/ISA/237) dated Nov. 2, 2015, by the U.S. Patent Office as the International Searching Authority for International Application No. PCT/US2015/043535.
Vasilevich et al., "Lessons from Natural Products Chemistry Can Offer Novel Approaches for Synthetic Chemistry in Drug Discovery", J. Med. Chem. 2012, pp. 7003-7009, vol. 55.
Rieser et al., "Determination of Absolute Configuration of Stereogenic Carbinol Centers in Annonaceous Acetogenins by $^1$H- and $^{19}$F-NMR Analysis of Mosher Ester Derivatives", J. Am. Chem. Soc., 1992, pp. 10203-10213, vol. 114, No. 26.
Montana et al., "Synthesis of 2,6-dioxatricyclo[3.3.1.0$^{3,7}$]nonanes by intramolecular haloetherification and/or transannular hydroxycyclization of alkenes in [4+3]-cycloadducts", Tetrahedron, 2009, pp. 5308-5321, vol. 65, issue 27.
Kigoshi et al., "Synthetic Studies on Aplyronine A, a Potent Antitumor Substance of Marine Origin: Stereocontrolled Synthesis of the C21—C34 Segment", Tetrahedron Letters, 1994, pp. 1247-1250, vol. 35, issue 8.
Bowers et al., "Thromboxane A, Analogues from 8-Oxabicyclo[3.2.1]oct-6-en-3-ones", J. Chem. Soc. Perkin Trans., 1987, pp. 1657-1666, vol. 1.
CAS, CAS Registry No. 1401932-23-7, 3 pages, Oct. 24, 2012.
Kvasnicaa et al., Synthesis of phthalates of betulinic acid and betulin with cytotoxic activity, Bioorganic & Medicinal Chemistry, 2005, pp. 3447-3454, vol. 13, No. 10.
Lautens et al., "Silacupration of oxabicyclic compounds. An interrupted ring opening reaction", J. Org. Chem., 1992, pp. 422-424, vol. 57, No. 2.
Vairaprakash et al., "Efficient resolution of (±)-trans-2,3-diphenylpiperazine using (1S)-(+)-10-camphorsulfonic acid and enrichment of enantiomeric purity of non-racemic 2,3-diphenylpiperazine using different achiral acids", Journal of Chemical Sciences, 2008, pp. 175-179, vol. 120.
Plet et al., "Synthesis of the bicyclic core of tagetitoxin", Chem. Commun., 2006, pp. 1197-1199.
PUBCHEM. SID 78854871. Jun. 12, 2009; p. 3, formula.

*Primary Examiner* — Rebecca L Anderson
*Assistant Examiner* — Karen Cheng
(74) *Attorney, Agent, or Firm* — Buchanan Ingersoll & Rooney PC

(57) ABSTRACT

The present invention relates to stereochemically defined polypropionates and methods for preparing and using the same. The stereochemically defined polypropionates may be useful in the synthesis of natural products and/or natural product-like libraries.

6 Claims, 1 Drawing Sheet

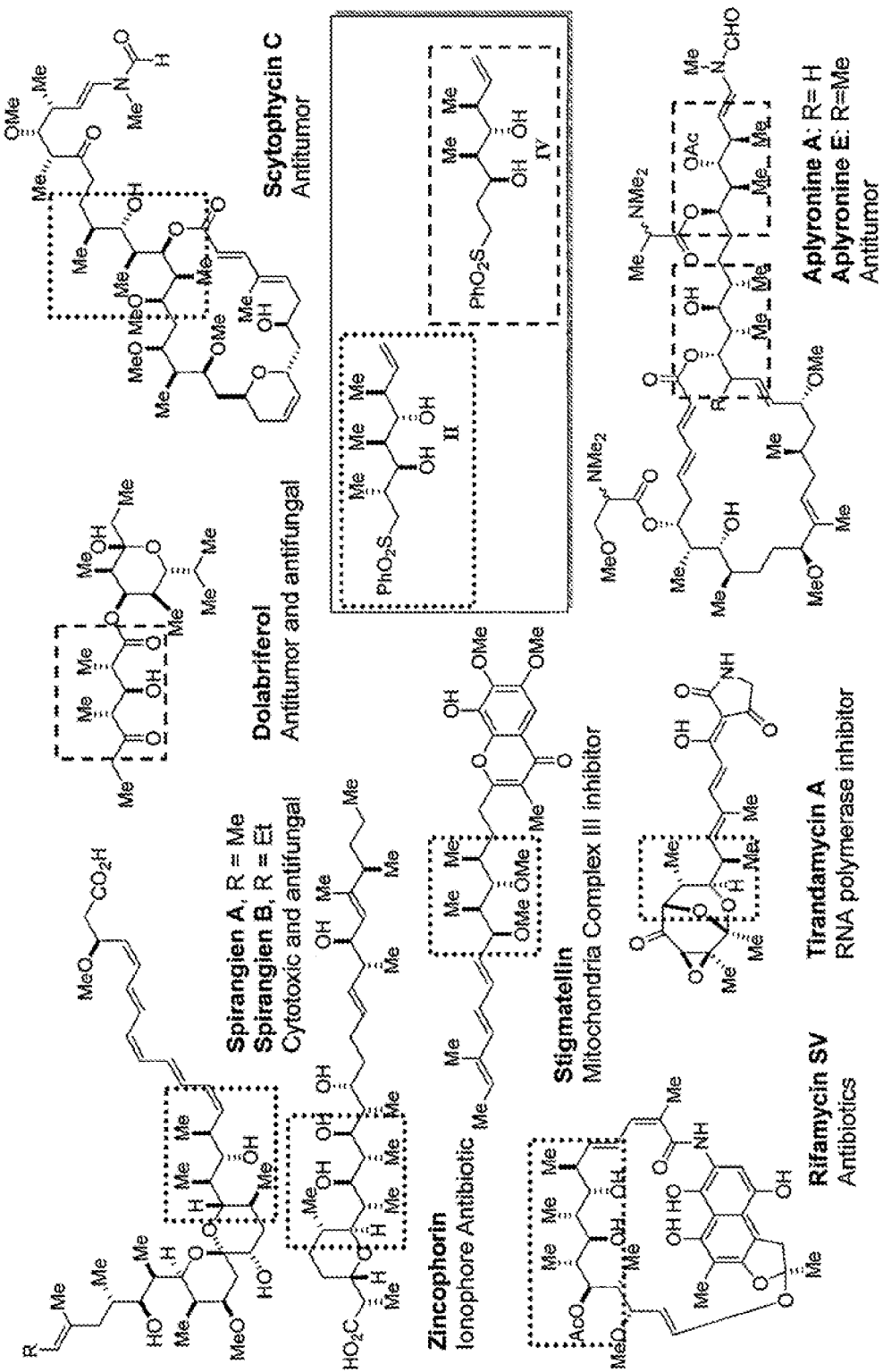

STEREOCHEMICALLY DEFINED POLYPROPIONATES AND METHODS FOR MAKING AND USING THE SAME

RELATED APPLICATION INFORMATION

This application claims the benefit of and priority to U.S. Provisional Application Ser. No. 62/032,757, filed Aug. 4, 2014, the disclosure of which is hereby incorporated by reference herein in its entirety.

FIELD

The present invention relates to stereochemically defined polypropionates and methods for preparing and using the same. The stereochemically defined polypropionates may be useful in the synthesis of natural products and/or natural product-like libraries.

BACKGROUND

Biologically active natural products have played a key role in the elucidation of cellular processes and biological mechanisms, and have been fruitful sources of therapeutic agents for many decades. Nearly half of the new chemical entities introduced in drug discovery between 1981 and 2002 were natural products or semi-synthetic analogs of natural products. (Vasilevich, N. I., et al., *J. Med. Chem.* 2012, 55, 7003-7009.) Polypropionate tetrads and pentads comprise a core structural element of many biologically active natural products.

SUMMARY

The present invention provides stereochemically defined polypropionates, including stereochemically defined pentads and tetrads, and methods for preparing and using the same.

In some embodiments provided is a compound of Formula II', III', IV', V', VI', and/or VII' having the following structure:

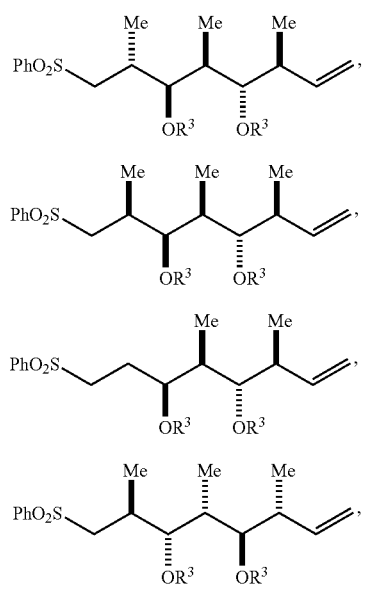

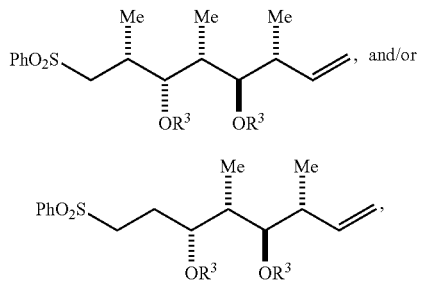

wherein:
Ph is phenyl; and
$R^3$ is each independently a hydrogen or an oxygen protecting group;
or a salt thereof.

In some embodiments, a compound of Formula II', III', IV', V', VI', and/or VII' can be used in a method of preparing a therapeutic.

In some embodiments, provided is a compound of Formula II, III, IV, V, VI, and/or VII having the following structure:

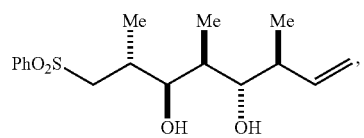

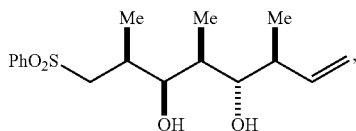

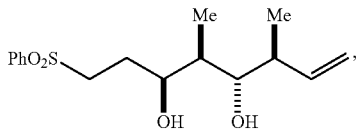

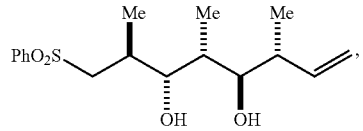

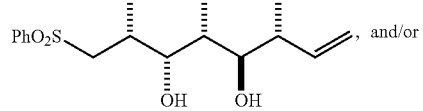

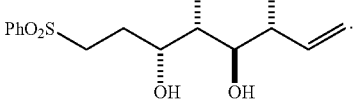

In some embodiments, the invention provides methods for preparing stereochemically defined polypropionate pentads, such as compounds of Formulas II', II, III', III, V', V, VI', and VI, and stereochemically defined polypropionate tetrads, such as compounds of Formulas IV', IV, VII', and VII, from a compound of Formula I having the following structure:

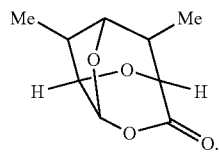

I

In certain embodiments, a compound of Formula II', II, III', III, IV', and/or IV is prepared from an enantiomerically pure compound of Formula Ia having the following structure:

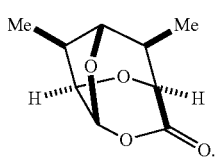

Ia

In some embodiments, a compound of Formula V', V, VI', VI, VII', and/or VII is prepared from an enantiomerically pure compound of Formula Ib having the following structure:

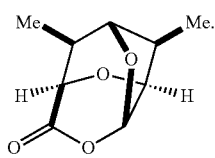

Ib

In some embodiments, methods for preparing compounds of Formulas Ia and Ib are provided. In some embodiments, compounds of Formulas Ia and Ib are prepared in optically active form.

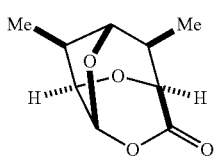

Ia

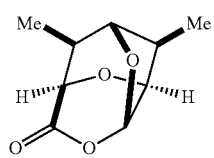

Ib

In some embodiments, compounds of Formulas Ia and/or Ib are prepared by oxidizing a compound of Formula 1 having the following structure:

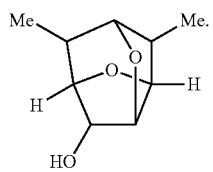

1

In certain embodiments, a compound of Formula Ia or Ib is prepared by oxidizing an optically active compound of Formula 1A or 1B, respectively, having the following structure:

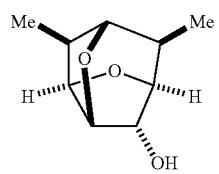

1A

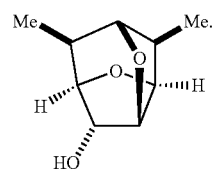

1B

In some embodiments, compounds of Formulas 1A and/or 1B can be obtained by resolving a mixture of compounds of Formulas 1A and 1B. In some embodiments, the resolution compounds of Formulas 1A and 1B can be achieved by selective crystallization and/or selective precipitation of a mixture of diastereomeric salts of Formulas 1A and 1B. In some embodiments, the mixture of diastereomeric salts of Formulas 1A and 1B can be obtained by forming a mixture of esters of Formulas 1A and 1B having free carboxylate groups, and then treating the mixture of esters of Formulas 1A and 1B having free carboxylate groups with a chiral amine-containing compound. In some embodiments, the mixture of esters of Formulas 1A and 1B having free carboxylate groups is obtained by treating a mixture of Formulas 1A and 1B with phthalic anhydride, to form a mixture of phthalates of Formulas 2A and 2B.

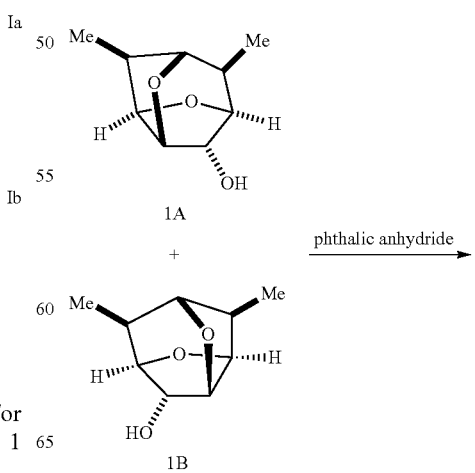

-continued

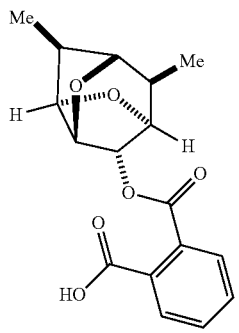

2A

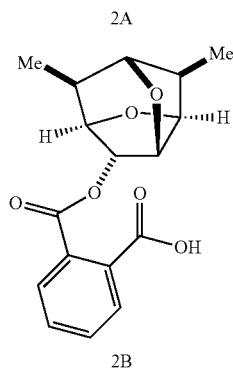

2B

In some embodiments, the mixture of phthalates of Formulas 2A and 2B is reacted with a chiral amine-containing compound to produce a mixture of diastereomeric salts. In some embodiments, the chiral amine is an enantiomer of α-methylbenzylamine. In some embodiments, the mixture of Formulas 2A and 2B is reacted with (R)-α-methylbenzylamine. In some embodiments, the mixture of Formulas 2A and 2B is reacted with (S)-α-methylbenzylamine.

In some embodiments, the mixture of diastereomeric salts is resolved by selective crystallization, or selective crystallization followed by recrystallization. In some embodiments, the mixture of Formulas 2A and 2B is treated with (S)-α-methylbenzylamine, and one of the diastereomeric salts is removed by filtration after it precipitates.

In some embodiments, a process for resolving enantiomers of a compound of Formula 1, is provided, the method comprising the steps of:

reacting the racemic compound of Formula 1 with phthalic anhydride to form a racemic mixture of phthalates of Formulas 2A and 2B having the structure:

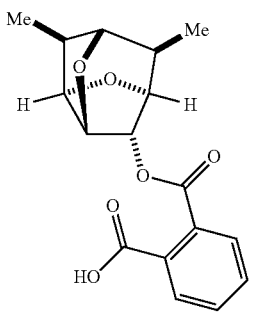

2A

-continued

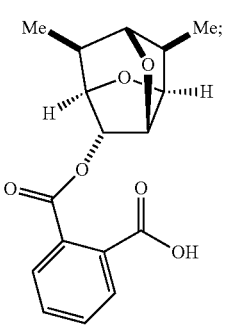

2B reacting the racemic mixture of phthalates of Formulas 2A and 2B with a first chiral amine in a solvent to form a pair of diastereomeric salts thereof in a solution;

precipitating a first diastereomeric salt of the pair of diastereomeric salts from the solution to provide an isolated first diasteriomeric salt and an second diastereomeric salt; and forming the enantiomers of the compound of Formula 1 from the isolated first diastereomeric salt and the second diastereomeric salt, thereby resolving the enantiomers of the compound of Formula 1.

In some embodiments, provided is a compound of Formula 1':

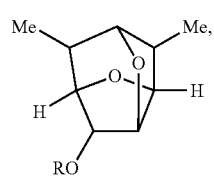

1' wherein:
R is hydrogen or —C(O)R$^1$, and
R$^1$ is selected from the group consisting of C$_1$-C$_8$alkyl, C$_1$-C$_8$alkenyl, aryl, and heteroaryl, R$^1$ may be unsubstituted or substituted from 1 to 3 times with independently selected C$_1$-C$_6$alkyl, hydroxy, hydroxyC$_1$-C$_6$alkyl, methoxy, methoxyC$_1$-C$_6$alkyl, halo, haloC$_1$-C$_6$alkyl, —C(O)NH$_2$, —NHCOOC$_1$-C$_6$alkyl, or —COOH group(s);
or a salt thereof.

In certain embodiments, provided is a compound of Formula 1 having the following structure:

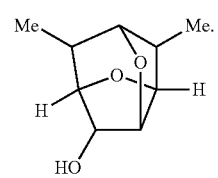

1

In some embodiments, a process for preparing a compound of Formula 1 is provided, the method comprising the steps of:

reacting 6,8-dimethyl-3,9-dioxatricyclo[3.3.1.0$^{2,4}$]nonan-7-one with a reducing agent to form an intermediate having the following structure:

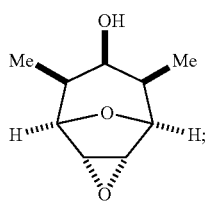

and reacting the intermediate with an acid to form the compound of Formula 1.

BRIEF DESCRIPTION OF THE DRAWINGS

FIG. 1 shows exemplary natural products and illustrates portions corresponding to a compound of Formula II or IV.

DETAILED DESCRIPTION

Compounds of this invention include those described generally herein, and are further illustrated by the embodiments, sub-embodiments, and species disclosed herein. As used herein, the following definitions shall apply unless otherwise indicated.

As described herein, compounds of the invention may optionally be substituted with one or more substituents, such as those illustrated generally herein, or as exemplified by particular classes, subclasses, and species of the invention. In general, the term "substituted" refers to the replacement of a hydrogen atom in a given structure with a specified substituent. Unless otherwise indicated, a substituted group may have a substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds.

"Isomers" refer to compounds having the same number and kind of atoms and hence the same molecular weight, but differing with respect to the arrangement or configuration of the atoms.

"Stereoisomers" refer to isomers that differ only in the arrangement of the atoms in space.

"Diastereoisomers" or "diastereomers" and grammatical variants thereof, as used herein, refer to stereoisomers that are not mirror images of each other.

"Enantiomers" and grammatical variants thereof, as used herein, refer to stereoisomers that are non-superimposable mirror images of one another.

Enantiomers include "enantiomerically pure" isomers that comprise substantially a single enantiomer, for example, greater than or equal to 90%, 92%, 95%, 98%, or 99%, or equal to 100% of a single enantiomer.

"Enantiomerically pure" as used herein refers a compound that comprises substantially a single enantiomer, for example, greater than or equal to 90%, 92%, 95%, 98%, or 99%, or equal to 100% of a single enantiomer. In some embodiments, a composition may comprise a compound that is enantiomerically pure.

"Stereomerically pure" as used herein means a compound or composition thereof that comprises one stereoisomer of a compound and is substantially free of other stereoisomers of that compound. For example, a stereomerically pure composition of a compound having one chiral center will be substantially free of the opposite enantiomer of the compound. A stereomerically pure composition of a compound having two chiral centers will be substantially free of diastereomers, and substantially free of the enantiomer, of the compound. A typical stereomerically pure compound comprises greater than about 80% by weight of one stereoisomer of the compound and less than about 20% by weight of other stereoisomers of the compound, more preferably greater than about 90% by weight of one stereoisomer of the compound and less than about 10% by weight of the other stereoisomers of the compound, even more preferably greater than about 95% by weight of one stereoisomer of the compound and less than about 5% by weight of the other stereoisomers of the compound, and most preferably greater than about 97% by weight of one stereoisomer of the compound and less than about 3% by weight of the other stereoisomers of the compound. See, e.g., U.S. Pat. No. 7,189,715.

"R" and "S" as terms describing isomers are descriptors of the stereochemical configuration at an asymmetrically substituted carbon atom. The designation of an asymmetrically substituted carbon atom as "R" or "S" is done by application of the Cahn-Ingold-Prelog priority rules, as are well known to those skilled in the art, and described in the International Union of Pure and Applied Chemistry (IUPAC) Rules for the Nomenclature of Organic Chemistry. Section E, Stereochemistry.

"Enantiomeric excess" (ee) of an enantiomer is [(the mole fraction of the major enantiomer) minus (the mole fraction of the minor enantiomer)]×100.

"Stable", as used herein, refers to compounds that are not substantially altered when subjected to conditions to allow for their production, detection, and preferably their recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week.

"Refluxing" as used herein refers to a technique in which vapors from a boiling liquid are condensed and returned to the mixture from which it came, typically by boiling the liquid in a vessel attached to a condenser.

"Powdered iron" or "iron powder" is iron having an average particle size of less than 0.1, 0.5, 1, 5, 10, 20, 50, 250, 500 or 1000 µm. Particle size can be measured using methods known in the art, e.g., mesh sizing, laser diffraction, etc.

"Zinc dust" is zinc having an average particle size of less than 0.001, 0.05, 0.1, 0.5, 1, 5, 10, 15 or 20 µm. "Zinc powder" is zinc having an average particle size of less than 200, 175, 150, 125, or 100 µm. Particle size can be measured using methods known in the art, e.g., mesh sizing, laser diffraction, etc.

An "organic" compound as used herein is a compound that contains carbon. Similarly, an "organic solvent" is a compound containing carbon that is useful as a solvent. An "inorganic" compound is a compound not containing carbon.

"Mineral acid" as used herein is the acid of an inorganic compound. Examples include, but are not limited to, hydrochloric acid (HCl), nitric acid ($HNO_3$), phosphoric acid ($H_3PO_4$), sulfuric acid ($H_2SO_4$), boric acid ($B(OH)_3$), hydrofluoric acid (HF), hydrobromic acid (HBr), perchoric acid ($HClO_4$), etc.

A "hydrocarbon" is an organic compound consisting of carbon and hydrogen atoms. Examples of hydrocarbons useful as "hydrocarbon solvents" include, but are not limited to, an "aromatic hydrocarbon solvent" such as benzene, toluene, xylenes, etc., and an "aliphatic hydrocarbon solvent" such as pentane, hexane, heptane, etc.

An "amine" or "amine base" as used herein refers to an organic compound having a basic nitrogen atom (R—NR'R"), and may be a primary (R—NH$_2$), secondary (R—NHR') or tertiary (R—NR'R") amine.

A "strong base" as used herein is a compound that is capable of deprotonating very weak acids. Examples of strong bases include, but are not limited to, hydroxides, alkoxides, and ammonia.

A "hydroxide" is the commonly known diatomic anion OH$^-$, or a salt thereof (typically an alkali metal or alkaline earth metal salt thereof). Examples of hydroxides include, but are not limited to, sodium hydroxide (NaCl), potassium hydroxide (KOH), lithium hydroxide (LiOH), and calcium hydroxide (CaOH).

An "alkoxide" is RO$^-$, the conjugate base of an alcohol. Examples include, but are not limited to, methoxide, ethoxide, and propoxide.

"Ar" or "aryl" refer to an aromatic carbocyclic moiety having one or more closed rings. Examples include, without limitation, phenyl, naphthyl, anthracenyl, phenanthracenyl, biphenyl, and pyrenyl.

"Heteroaryl" refers to a cyclic moiety having one or more closed rings, with one or more heteroatoms (for example, oxygen, nitrogen or sulfur) in at least one of the rings, wherein at least one of the rings is aromatic, and wherein the ring or rings may independently be fused, and/or bridged. Examples include, without limitation phenyl, thiophenyl, triazolyl, pyridinyl, pyrimidinyl, pyridazinyl, pyrazinyl, quinolinyl, isoquinolinyl, indolyl, furyl, thienyl, pyrazolyl, quinoxalinyl, pyrrolyl, indazolyl, thieno[2,3-c]pyrazolyl, benzofuryl, pyrazolo[1,5-a]pyridyl, thiophenylpyrazolyl, benzothienyl, benzothiazolyl, thiazolyl, 2-phenylthiazolyl, and isoxazolyl.

"Alkyl" or "alkyl group," as used herein, means a straight-chain (i.e., unbranched), branched, or cyclic hydrocarbon chain that is completely saturated. In some embodiments, alkyl groups contain 1, 2, or 3, to 4, 5, 6, 7, or 8 carbon atoms (e.g., $C_{1-4}$, $C_{2-4}$, $C_{3-4}$, $C_{1-5}$, $C_{2-5}$, $C_{3-5}$, $C_{1-6}$, $C_{2-6}$, $C_{3-6}$, $C_{2-7}$, $C_1$, $C_{4-8}$, etc.). In some embodiments, alkyl groups contain 1-8 carbon atoms. In certain embodiments, alkyl groups contain 1-6 carbon atoms. In still other embodiments, alkyl groups contain 2-3 carbon atoms, and in yet other embodiments alkyl groups contain 1-4 carbon atoms. In certain embodiments, the term "alkyl" or "alkyl group" refers to a cycloalkyl group, also known as carbocycle. Non-limiting examples of exemplary alkyl groups include methyl, ethyl, propyl, isopropyl, butyl, cyclopropyl and cyclohexyl.

"Alkenyl" or "alkenyl group," as used herein, refers to a straight-chain (i.e., unbranched), branched, or cyclic hydrocarbon chain that has one or more double bonds. In certain embodiments, alkenyl groups contain 1-8 carbon atoms. In certain embodiments, alkenyl groups contain 1-6 carbon atoms. In still other embodiments, alkenyl groups contain 1-4 carbon atoms, and in yet other embodiments alkenyl groups contain 2-3 carbon atoms. According to another aspect, the term alkenyl refers to a straight chain hydrocarbon having two double bonds, also referred to as "diene." In other embodiments, the term "alkenyl" or "alkenyl group" refers to a cycloalkenyl group. Non-limiting examples of exemplary alkenyl groups include —CH=CH$_2$, —CH$_2$CH=CH$_2$ (also referred to as allyl), —CH=CH$_3$, —CH$_2$CH=CH=CH$_2$, —CH$_2$CH=CHCH$_3$, —CH=CH$_2$CH$_2$CH$_3$, —CH=CH$_2$CH=CH$_2$, and cyclobutenyl.

"Alkoxy", or "alkylthio", as used herein, refers to an alkyl group, as previously defined, attached to the principal carbon chain through an oxygen ("alkoxy") or sulfur ("alkylthio") atom.

"Methylene", "ethylene", and "propylene" as used herein refer to the bivalent moieties —CH$_2$—, —CH$_2$CH$_2$—, and —CH$_2$CH$_2$CH$_2$—, respectively.

"Ethenylene", "propenylene", and "butenylene" as used herein refer to the bivalent moieties —CH=CH—, —CH=CHCH$_2$—, —CH$_2$CH=CH—, —CH=CHCH$_2$CH$_2$—, —CH$_2$CH=CH$_2$CH$_2$—, and —CH$_2$CH$_2$CH=CH—, where each ethenylene, propenylene, and butenylene group can be in the cis or trans configuration. In certain embodiments, an ethenylene, propenylene, or butenylene group can be in the trans configuration.

"Alkylidene" refers to a bivalent hydrocarbon group formed by mono or dialkyl substitution of methylene. In certain embodiments, an alkylidene group has 1-6 carbon atoms. In other embodiments, an alkylidene group has 2-6, 1-5, 2-4, or 1-3 carbon atoms. Such groups include propylidene (CH$_3$CH$_2$CH=), ethylidene (CH$_3$CH=), and isopropylidene (CH$_3$(CH$_3$)CH=), and the like.

"Alkenylidene" refers to a bivalent hydrocarbon group having one or more double bonds formed by mono or dialkenyl substitution of methylene. In certain embodiments, an alkenylidene group has 2-6 carbon atoms. In other embodiments, an alkenylidene group has 2-6, 2-5, 2-4, or 2-3 carbon atoms. According to one aspect, an alkenylidene has two double bonds. Exemplary alkenylidene groups include CH$_3$CH=C=, CH$_2$=CHCH=, CH$_2$=CHCH$_2$CH=, and CH$_2$=CHCH$_2$CH=CHCH=.

"$C_{1-6}$ alkyl ester or amide" refers to a $C_{1-6}$ alkyl ester or a $C_{1-6}$ alkyl amide where each $C_{1-6}$ alkyl group is as defined above. Such $C_{1-6}$ alkyl ester groups are of the formula ($C_{1-6}$ alkyl)OC(=O)— or ($C_{1-6}$ alkyl)C(=O)O—. Such $C_{1-6}$ alkyl amide groups are of the formula ($C_{1-6}$ alkyl)NHC(=O)— or ($C_{1-6}$ alkyl)C(=O)NH—.

"$C_{2-6}$ alkenyl ester or amide" refers to a $C_{2-6}$ alkenyl ester or a $C_{2-6}$ alkenyl amide where each $C_{2-6}$ alkenyl group is as defined above. Such $C_{2-6}$ alkenyl ester groups are of the formula ($C_{2-6}$ alkenyl)OC(=O)— or ($C_{2-6}$ alkenyl)C(=O)O—. Such $C_{2-6}$ alkenyl amide groups are of the formula ($C_{2-6}$ alkenyl)NHC(=O)— or ($C_{2-6}$ alkenyl)C(=O)NH—.

"Halo" refers to fluoro, chloro, bromo or iodo.

"Haloalkyl" refers to an alkyl group substituted with one or more halo atoms (e.g., fluoro, chloro, bromo, and/or iodo atoms). For example, "fluoromethyl" refers to a methyl group substituted with one or more fluoro atoms (e.g., monofluoromethyl, difluoromethyl, and trifluoromethyl).

"Hydroxyalkyl" refers to an alkyl group substituted with a hydroxyl group (—OH).

"Fluoromethoxy" as used herein, refers to a fluoromethyl group, as previously defined, attached to the principal carbon chain through an oxygen atom.

"Protecting group" as used herein, is meant that a particular functional moiety, e.g., O, S, or N, is temporarily blocked so that a reaction can be carried out selectively at another reactive site in a multifunctional compound. For example, in certain embodiments, as detailed herein, certain exemplary oxygen protecting groups are utilized. Oxygen protecting groups include, but are not limited to, groups bonded to the oxygen to form an ether, such as methyl, substituted methyl (e.g., Trt (triphenylmethyl), MOM (methoxymethyl), MTM (methylthiomethyl), BOM (benzyloxymethyl), PMBM or MPM (p-methoxybenzyloxymethyl)), substituted ethyl (e.g., 2-(trimethylsilyl)ethyl), benzyl, substituted benzyl (e.g., para-methoxybenzyl), silyl (e.g., TMS (trimethylsilyl), TES (triethylsilyl), TIPS (triisopropylsilyl), TBDMS (t-butyldimethylsilyl), tribenzylsilyl, TBDPS (t-butyldiphenyl silyl), 2-trimethylsilylprop-2-enyl, t-butyl, tetrahydropyranyl, allyl, etc.

In some embodiments, a compound of the present invention may be provided as a salt, such as a pharmaceutically acceptable salt. Pharmaceutically acceptable salts are salts that retain the desired biological activity of the parent compound and do not impart undesired toxicological effects. Specific examples of pharmaceutically acceptable salts include inorganic acid salts (such as sulfates, nitrates, perchlorates, phosphates, carbonates, bicarbonates, hydrofluorides, hydrochlorides, hydrobromides and hydroiodides), organic carboxylates (such as acetates, oxalates, maleates, tartrates, fumarates and citrates), organic sulfonates (such as methanesulfonates, trifluoromethanesulfonates, ethanesulfonates, benzenesulfonates, toluenesulfonates and camphorsulfonates), amino acid salts (such as aspartates and glutamates), quaternary amine salts, alkali metal salts (such as sodium salts and potassium salts) and alkali earth metal salts (such as magnesium salts and calcium salts).

Unless indicated otherwise, nomenclature used to describe chemical groups or moieties as used herein follow the convention where, reading the name from left to right, the point of attachment to the rest of the molecule is at the right-hand side of the name. For example, the group "($C_{1-3}$ alkoxy)$C_{1-3}$ alkyl," is attached to the rest of the molecule at the alkyl end. Further examples include methoxyethyl, where the point of attachment is at the ethyl end, and methylamino, where the point of attachment is at the amine end.

Unless indicated otherwise, where a mono or bivalent group is described by its chemical formula, including one or two terminal bond moieties indicated by "-," it will be understood that the attachment is read from left to right.

Unless otherwise stated, structures depicted herein are meant to include all enantiomeric, diastereomeric, and geometric (or conformational) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention.

Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^3$C- or $^{14}$C-enriched carbon are within the scope of this invention. Such compounds are useful, for example, as analytical tools or probes in biological assays.

Provided herein according to some embodiments is a compound of Formula 1':

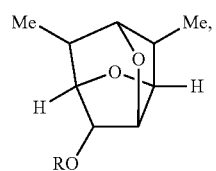

wherein:
R is hydrogen or —C(O)R$^1$, and
R$^1$ is selected from the group consisting of $C_1$-$C_8$alkyl, $C_1$-$C_8$alkenyl, aryl, and heteroaryl, R$^1$ may be unsubstituted or substituted from 1 to 3 times with independently selected $C_1$-$C_6$alkyl, hydroxy, hydroxy$C_1$-$C_6$alkyl, methoxy, methoxy$C_1$-$C_6$alkyl, halo, halo$C_1$-$C_6$alkyl, —C(O)NH$_2$, —NHCOO$C_1$-$C_6$alkyl, or —COOH group(s);
or a salt thereof.

In some embodiments, a compound of Formula 1' has the stereochemistry of Formula 1A':

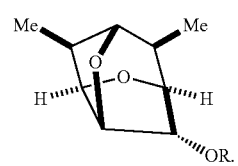

In some embodiments, a compound of Formula I has the stereochemistry of Formula IB:

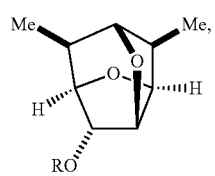

According to some embodiments, R in a compound of Formula 1' is a hydrogen and the compound has a structure of Formula 1:

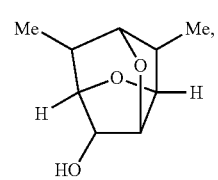

or a salt thereof.
In some embodiments, a compound of Formula 1 has the stereochemistry of Formula 1A:

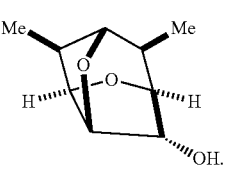

In some embodiments, a compound of Formula 1 has the stereochemistry of Formula 1B:

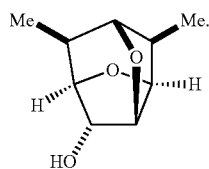

According to some embodiments, R in a compound of Formula 1' is —C(O)R¹ or a salt thereof. In certain embodiments, in a compound of Formula 1', R is —C(O)R¹ and R¹ is substituted with —COOH, or a salt thereof.

Provided according to further embodiments of the present invention is a compound of Formula 2:

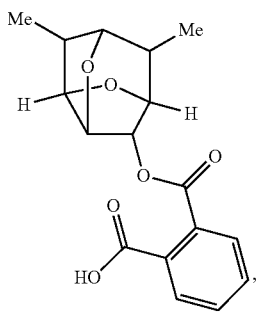

or a salt thereof.

In some embodiments, a compound of Formula 2 has the stereochemistry of Formula 2A:

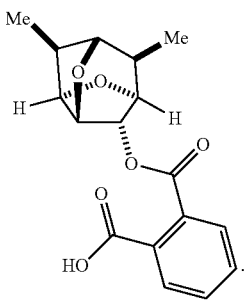

In some embodiments, a compound of Formula 2 has the stereochemistry of Formula 2B:

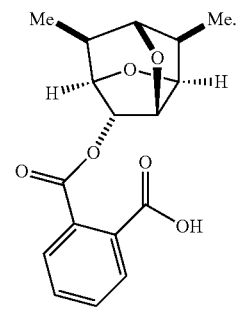

In some embodiments, a process for preparing a compound of Formula 1 is provided. The process may comprise reacting 6,8-dimethyl-3,9-dioxatricyclo[3.3.1.0$^{2,4}$]nonan-7-one with a reducing agent to form an intermediate having the following structure:

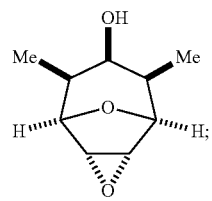

reacting the intermediate with an acid to form the compound of Formula 1.

Exemplary reducing agents that may be used in preparing a compound of Formula 1 include, but are not limited to, hydrides, such as sodium borohydride, potassium borohydride, lithium borohydride, lithium aluminum hydride, and sodium cyanoborohydride. In some embodiments, the reducing agent may be sodium borohydride.

Exemplary acids that may be used in preparing a compound of Formula 1 include, but are not limited to, hydrochloric acid, hydrofluoric acid, hydrobromic acid, hydroiodic acid, sulfuric acid, nitric acid, citric acid, glycolic acid, formic acid, oxalic acid, boric acid, and/or acetic acid. In some embodiments, the acid may be hydrochloric acid.

According to some embodiments, a process for resolving enantiomers of the compound of Formula 1 is provided. The process may be a process for resolving a mixture of compounds of Formulas 1A and 1B. In some embodiments, the resolution compounds of Formulas 1A and 1B may be achieved by selective crystallization and/or selective precipitation of a mixture of diastereomeric salts of Formulas 1A and 1B. In some embodiments, the mixture of diastereomeric salts of Formulas 1A and 1B may be obtained by forming a mixture of esters of Formulas 1A and 1B having free carboxylate groups, and then by treating the mixture of esters of Formulas 1A and 1B having free carboxylate groups with a chiral amine-containing compound (i.e., a chiral amine), such as, for example, α-methylbenzylamine.

In some embodiments, a process for resolving enantiomers of the compound of Formula I may comprise reacting the racemic compound of Formula 1:

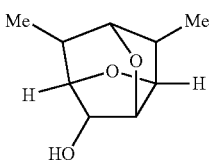

with phthalic anhydride to form a racemic mixture of phthalates of Formulas 2A and 2A:

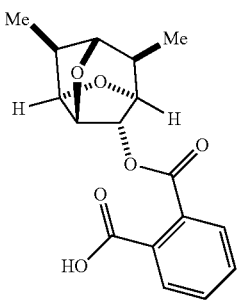

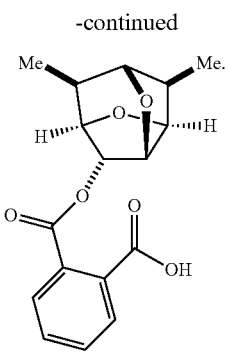

2B

The racemic mixture of phthalates of Formula 2 may be reacted with a first chiral amine in a solvent to form a pair of diastereomeric salts thereof in a solution, and a first diastereomeric salt of the pair of diastereomeric salts may be precipitated from the solution to provide an isolated first diastereomeric salt and an second diastereomeric salt. Enantiomers of the compound of Formula 1 may then be formed from the isolated first diastereomeric salt and the second diastereomeric salt, thereby resolving the enantiomers of the compound of Formula 1.

In some embodiments, prior to reacting the racemic mixture of phthalates of Formula 2 with the first chiral amine in the solvent to form the pair of diastereomeric salts thereof in the solution, the racemic mixture of phthalates of Formula 2 may be dissolved in the solvent. In some embodiments, the racemic mixture of phthalates of Formula 2 may be dissolved in the solvent at a volume ratio in a range of about 1:12 to about 1:20 (phthalates:solvent), such as, but not limited to, at a volume ratio of about 1:12, 1:13, 1:14, 1:15, 1:16, 1:17, 1:18, 1:19, or 1:20. In some embodiments, the volume ratio may be about 1:15. In some embodiments, the solvent may be acetone.

In some embodiments, the first chiral amine is (S)-α-methylbenzylamine. Reacting (S)-α-methylbenzylamine with the racemic mixture of phthalates of Formula 2 in a solvent may precipitate the first diastereomeric salt of the pair of diastereomeric salts from the solution, thereby providing the isolated first diastereomeric salt. In some embodiments, the isolated first diastereomeric salt may have the following structure of Formula 2B':

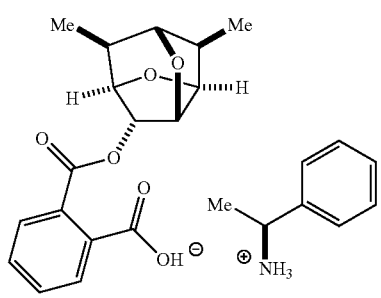

2B'

In some embodiments, a process for resolving enantiomers of the compound of Formula 1 may comprise treating the isolated first diastereomeric salt with a base to form a first enantiomeric compound of Formula 1. Exemplary bases include, but are not limited to, sodium hydroxide, potassium hydroxide, barium hydroxide, calcium hydroxide, cesium hydroxide, and/or alkoxides, such as, for example sodium, potassium, and/or lithium methoxide, ethoxide, propoxide, and/or n-butoxide. In some embodiments, the isolated first diastereomeric salt may be a compound of Formula 2B' and the first enantiomeric compound of Formula 1 may be a compound of Formula 1B having the following structure:

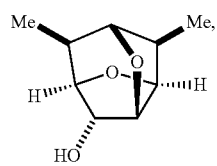

1B or a salt thereof. The first diastereomeric salt may be in crystalline form. Accordingly, the process may comprise one or more crystallization steps (e.g., crystallizing and/or recrystallizing steps).

In some embodiments, a process for resolving enantiomers of the compound of Formula 1 may comprise separating the first diastereomeric salt from the solution to separately provide the isolated first diastereomeric salt and the second diastereomeric salt. Exemplary methods of separating will be known to those of skill in the art and include, but are not limited to, filtering the solution to separately provide the isolated first diastereomeric salt and the second diastereomeric salt.

A process for resolving enantiomers of the compound of Formula 1 may comprise acidifying the second diastereomeric salt to form a free phthalate. The second diastereomeric salt may have the following structure of Formula 2A':

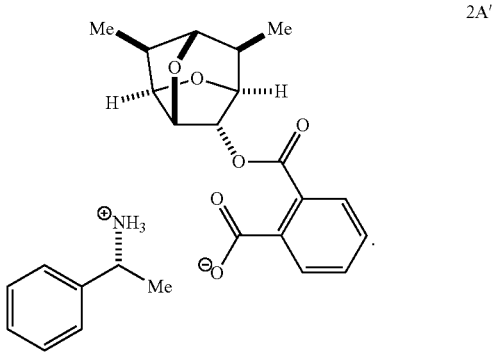

2A'

The free phthalate may be reacted with a second chiral amine to reform the second diastereomeric salt in a solution. In some embodiments, the second chiral amine is (R)-α-methylbenzylamine. The second diastereomeric salt may be precipitated from the solution to form an isolated second diastereomeric salt. In some embodiments, the isolated second diastereomeric salt may be a compound of Formula 2A'. A second enantiomeric compound of Formula 1 may be from the isolated second diastereomeric salt.

In some embodiments, prior to reacting the free phthalate with the second chiral amine to reform the second diastereomeric salt in the solution, the free phthalate may be dissolved in a solvent. In some embodiments, the free phthalate may be dissolved in the solvent at a volume ratio in a range of about 1:12 to about 1:20 (phthalate:solvent), such as, but not limited to, at a volume ratio of about 1:12, 1:13, 1:14, 1:15, 1:16, 1:17, 1:18, 1:19, or 1:20. In some embodiments, the volume ratio may be about 1:15. In some embodiments, the solvent may be acetone.

In some embodiments, a process for resolving enantiomers of the compound of Formula 1 may comprise treating the isolated second diastereomeric salt with a base to form a second enantiomeric compound of Formula 1. Exemplary bases include, but are not limited to, sodium hydroxide, potassium hydroxide, barium hydroxide, calcium hydroxide, cesium hydroxide, and/or alkoxides, such as, for example sodium, potassium, and/or lithium methoxide, ethoxide, propoxide, and/or n-butoxide. In some embodiments, the isolated second diastereomeric salt may be a compound of Formula 2A' and the second enantiomeric compound of Formula 1 may be a compound of Formula 1A having the following structure:

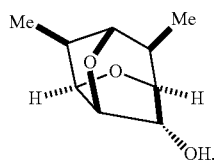

1A

In some embodiments, the second diastereomeric salt may be in crystalline form. Accordingly, the process may comprise one or more crystallization steps (e.g., crystallizing and/or recrystallizing steps).

Provided according to further embodiments of the present invention is a compound of Formula I having the structure:

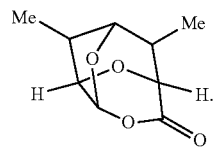

I

In some embodiments, a compound of Formula I may have the stereochemistry of a compound of Formula Ia:

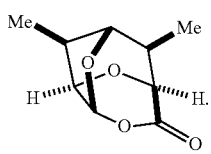

Ia

In some embodiments, a compound of Formula I may have the stereochemistry of a compound of Formula Ib:

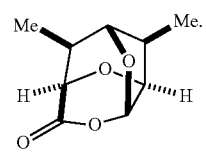

Ib

According to some embodiments, a process for preparing a compound of Formula I may be provided. The process may comprise treating a compound of Formula 1:

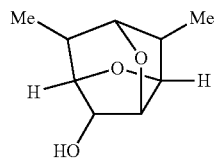

1 with an oxidizing agent to form the compound of Formula I. Exemplary oxidizing agents include, but are not limited to, peracetic acid, perbenzoic acid, m-chloroperbenzoic acid, perphthalic acid, performic acid, trifluoroperacetic acid, sulfur trioxide pyridine complex, hydrogen peroxide, pyridinium dichromate (PDC), and/or pyridinium chlorochromate (PCC). In some embodiments, the oxidizing agent may be m-chloroperbenzoic acid. In some embodiments, the oxidizing agent may be a sulfur trioxide pyridine complex.

A catalyst may optionally be present during the treatment of a compound of Formula 1 with an oxidizing agent to form a compound of Formula I. Exemplary catalysts include, but are not limited to, 2,2,6,6-tetramethyl-1-piperidinyloxy, 4-hydroxy-2,2,6,6-tetramethyl-1-piperidinyloxy, 4-(2-chloroacetamido)-2,2,6,6-tetramethyl-1-piperidinyloxy, and/or 4-(acetylamino)-2,2,6,6-tetramethyl-piperidinyloxy. In some embodiments, the catalyst may be 2,2,6,6-tetramethyl-1-piperidinyloxy. In certain embodiments, the catalyst may be 2,2,6,6-tetramethyl-1-piperidinyloxy and the oxidizing agent may be m-chloroperbenzoic acid.

In some embodiments, a process for preparing a compound of Formula I may form an intermediate ketone having the following structure of Formula Ia":

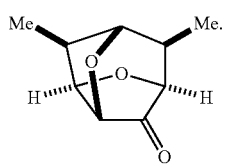

Ia"

In some embodiments, a process for preparing a compound of Formula I may form an intermediate ketone having the following structure of Formula Ib":

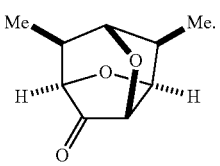

Ib"

In some embodiments, a compound of Formula 1 may be reacted with an oxidizing agent, such as, for example, a sulfur trioxide pyridine complex, to form the intermediate ketone of Formula Ia" and/or Formula Ib". The intermediate ketone of Formula Ia" and/or Formula Ib" may be then reacted with an oxidizing agent, such as, for example, m-chloroperbenzoic acid, optionally in the presence of a catalyst.

In some embodiments, a process for preparing a compound of Formula I may comprise treating a compound of Formula 1a:

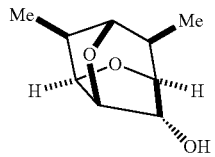

1a with an oxidizing agent, optionally in the presence of a catalyst, to form a compound of Formula Ia:

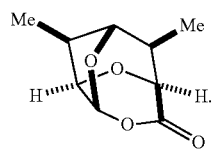

Ia

In some embodiments, a process for preparing a compound of Formula I may comprise treating a compound of Formula 1b:

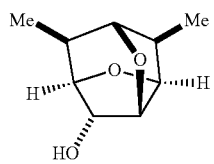

1b with an oxidizing agent, optionally in the presence of a catalyst, to form a compound of Formula Ib:

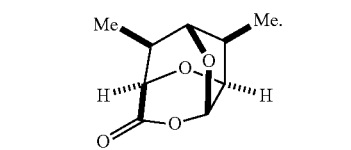

Ib

According to some embodiments, provided is a compound of Formula II′, III′, IV′, V′, VI′, and/or VII′ having the following structure:

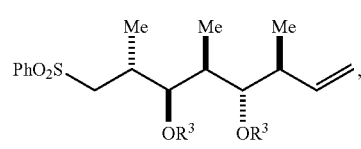

II′

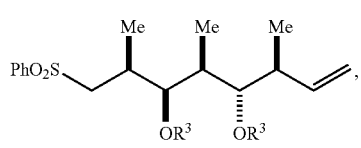

III′

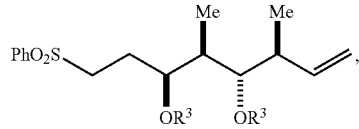

IV′

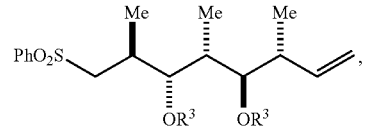

V′

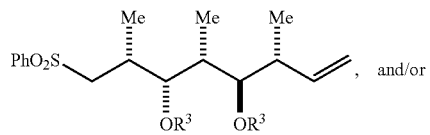

VI′, and/or

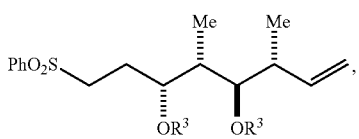

VII′ wherein:

Ph is phenyl; and $R^3$ is each independently a hydrogen or an oxygen protecting group;

or a salt thereof.

In some embodiments, at least one $R^3$ is hydrogen in a compound of Formula II′, III′, IV′, V′, VI′, or VII′. In some embodiments, at least one $R^3$ is an oxygen protecting group in a compound of Formula II′, III′, IV′, V′, VI′, or VII′. In some embodiments, at least one $R^3$ is hydrogen and at least one $R^3$ is an oxygen protecting group in a compound of Formula II′, III′, IV′, V′, VI′, or VII′. In some embodiments, two or more $R^3$ are hydrogen in a compound of Formula II′, III′, IV′, V′, VI′, or VII′. In some embodiments, two or more $R^3$ are an oxygen protecting group that may be the same as or different than another $R^3$ in a compound of Formula II′, III′, IV′, V′, VI′, or VII′. In certain embodiments, all $R^3$ are hydrogen in a compound of Formula II′, III′, IV′, V′, VI′, or VII′. In certain embodiments, all $R^3$ are an oxygen protecting group that may be the same as or different than another $R^3$ in a compound of Formula II, III′, IV′, V′, VI′, or VII′.

Exemplary oxygen protecting groups include, but are not limited to, those described herein, such as Trt (triphenylmethyl), MOM (methoxymethyl), MTM (methylthiomethyl), BOM (benzyloxymethyl), PMBM or MPM (p-methoxybenzyloxymethyl)), substituted ethyl (e.g., 2-(trimethylsilyl) ethyl), benzyl, substituted benzyl (e.g., para-methoxybenzyl), silyl (e.g., TMS (trimethylsilyl), TES (triethylsilyl), TIPS (triisopropylsilyl), TBDMS (t-butyldimethylsilyl), tribenzylsilyl, TBDPS (t-butyldiphenyl silyl), 2-trimethylsilylprop-2-enyl, t-butyl, tetrahydropyranyl, and/or allyl. In some embodiments, the oxygen protecting group is triethylsilyl (TES).

In some embodiments, provided is a compound of Formula II, III, IV, V, VI, and/or VII having the following structure:

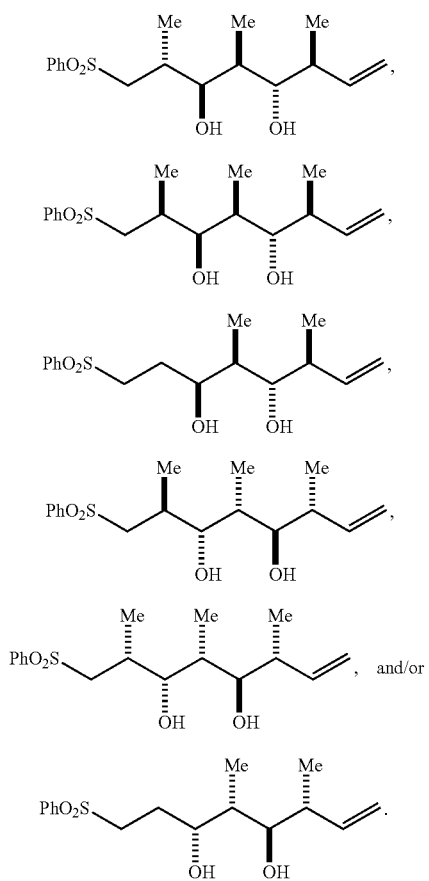

II

III

IV

V

VI

, and/or

VII

Provided in some embodiments is a method for preparing a compound of Formula II', II, III', III, IV', IV, V', V, VI', VI, VII', and/or VII. Described below are exemplary processes for preparing a compound of Formula II, III, IV, V, VI, and VII. As those skilled in the art will readily appreciate the exemplary processes may be modified, such as by not removing the oxygen protecting group to prepare a compound of Formula II', III', IV', V', VI', or VII'. Exemplary reducing agents and oxygen protecting that may be used in a method for preparing a compound of Formula II', II, III', III, IV', IV, V', V, VI', VI, VII', and/or VII include those described herein.

In some embodiments, a process for preparing a compound of Formula IV is provided. A process for preparing a compound of Formula IV may comprise providing a mixture of a dialkyl((arylsulfonyl)methyl)phosphonate and a compound of Formula I having the stereochemistry of a compound of Formula Ia:

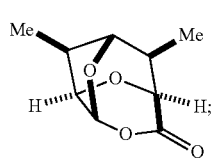

Ia reacting the mixture with an alkoxide in a polar protic solvent to form a compound of Formula AAAA having the structure:

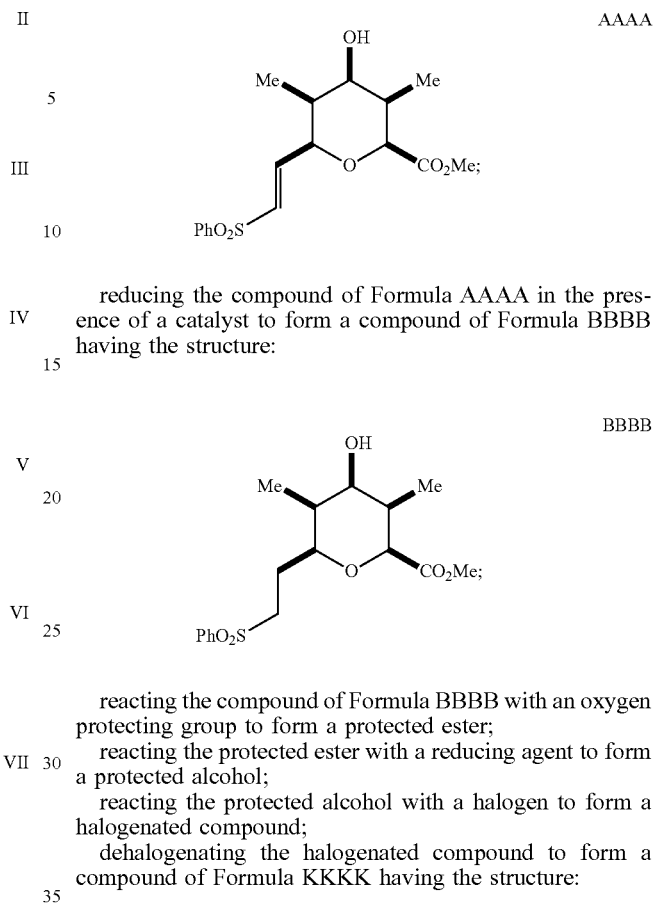

AAAA reducing the compound of Formula AAAA in the presence of a catalyst to form a compound of Formula BBBB having the structure:

BBBB reacting the compound of Formula BBBB with an oxygen protecting group to form a protected ester;
reacting the protected ester with a reducing agent to form a protected alcohol;
reacting the protected alcohol with a halogen to form a halogenated compound;
dehalogenating the halogenated compound to form a compound of Formula KKKK having the structure:

KKKK wherein:
Ph is a phenyl group; and
$R^2$ is an oxygen protecting group; and
removing the oxygen protecting group of the compound of Formula KKKK to form the compound of Formula IV.

In some embodiments, a process for preparing a compound of Formula III may be provided. A process for preparing a compound of Formula III may comprise providing a mixture of a dialkyl((arylsulfonyl)methyl)phosphonate and a compound of Formula I having the stereochemistry of a compound of Formula Ia:

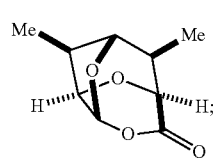

Ia reacting the mixture with an alkoxide in a polar protic solvent to form a compound of Formula AAAA having the structure:

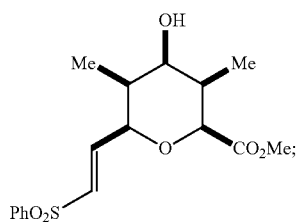

AAAA reacting the compound of Formula AAAA with an oxygen protecting group to form a protected ester;
reacting the protected ester with a reducing agent to form a protected alcohol;
reacting the protected alcohol with a halogen to form a halogenated compound;
dehalogenating the halogenated compound to form a compound of Formula LLLL having the structure:

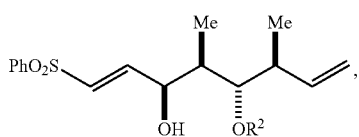

LLLL wherein:
Ph is a phenyl group; and
$R^2$ is an oxygen protecting group; and
reacting the compound of Formula LLLL with a methyl-lithium-lithium bromide complex to form the compound of Formula III.

In some embodiments, a process for preparing a compound of Formula II may be provided. A process for preparing a compound of Formula II may comprise providing a mixture of a dialkyl((arylsulfonyl)methyl)phosphonate and a compound of Formula I having the stereochemistry of a compound of Formula Ia:

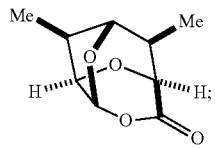

Ia reacting the mixture with an alkoxide in a polar protic solvent to form a compound of Formula AAAA having the structure:

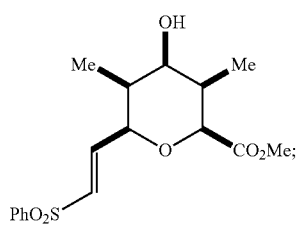

AAAA reacting the compound of Formula AAAA with an oxygen protecting group to form a protected ester;
reacting the protected ester with a reducing agent to form a protected alcohol;
reacting the protected alcohol with a halogen to form a halogenated compound;
dehalogenating the halogenated compound to form a compound of Formula LLLL having the structure:

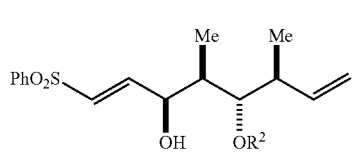

LLLL wherein:
Ph is a phenyl group; and
$R^2$ is an oxygen protecting group; and
reacting the compound of Formula LLLL with methyl-lithium in the presence of copper to form the compound of Formula II.

In some embodiments, a process for preparing a compound of Formula VII may be provided. A process for preparing a compound of Formula VII may comprise providing a mixture of a dialkyl((arylsulfonyl)methyl)phosphonate and a compound of Formula I having the stereochemistry of a compound of Formula Ib:

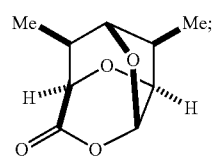

Ib reacting the mixture with an alkoxide in a polar protic solvent to form a compound of Formula MMMM having the structure:

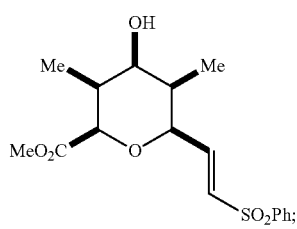

MMMM reducing the compound of Formula MMMM in the presence of a catalyst to form a compound of Formula NNNN having the structure:

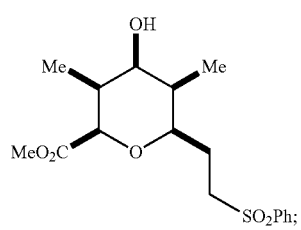

NNNN reacting the compound of Formula NNNN with an oxygen protecting group to form a protected ester;
reacting the protected ester with a reducing agent to form a protected alcohol;

reacting the protected alcohol with a halogen to form a halogenated compound;

dehalogenating the halogenated compound to form a compound of Formula OOOO having the structure:

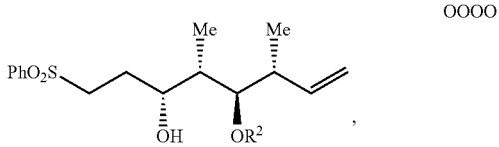

wherein:
Ph is a phenyl group; and
R² is an oxygen protecting group; and removing the oxygen protecting group of the compound of Formula OOOO to form the compound of Formula VII.

In some embodiments, a process for preparing a compound of Formula VI may be provided. A process for preparing a compound of Formula VI may comprise providing a mixture of a dialkyl((arylsulfonyl)methyl)phosphonate and a compound of Formula I having the stereochemistry of a compound of Formula Ib:

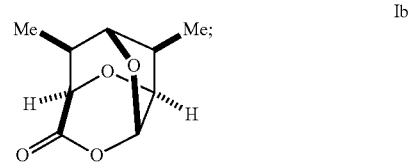 [SMILES: C[C@@H]1[C@@H]2O[C@H]3OC(=O)[C@H](O[C@H]31)[C@H]2C]

reacting the mixture with an alkoxide in a polar protic solvent to form a compound of Formula MMMM having the structure:

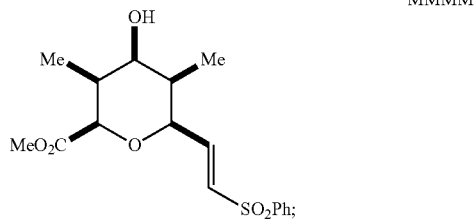

reacting the compound of Formula MMMM with an oxygen protecting group to form a protected ester;

reacting the protected ester with a reducing agent to form a protected alcohol;

reacting the protected alcohol with a halogen to form a halogenated compound;

dehalogenating the halogenated compound to form a compound of Formula PPPP having the structure:

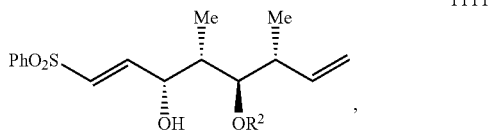

wherein:
Ph is a phenyl group; and
R² is an oxygen protecting group; and reacting the compound of Formula PPPP with a methyllithium-lithium bromide complex to form the compound of Formula VI.

In some embodiments, a process for preparing a compound of Formula V may be provided. A process for preparing a compound of Formula V may comprise providing a mixture of a dialkyl((arylsulfonyl)methyl)phosphonate and a compound of Formula I having the stereochemistry of a compound of Formula Ib:

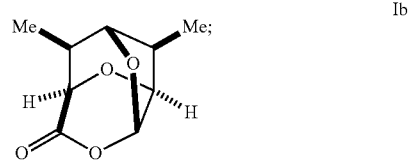 [SMILES: C[C@@H]1[C@@H]2O[C@H]3OC(=O)[C@H](O[C@H]31)[C@H]2C]

reacting the mixture with an alkoxide in a polar protic solvent to form a compound of Formula MMMM having the structure:

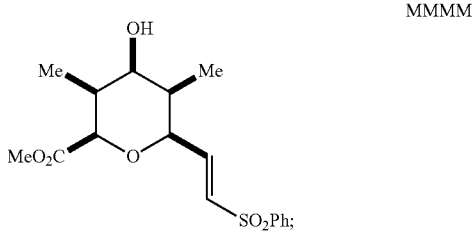

reacting the compound of Formula MMMM with an oxygen protecting group to form a protected ester;

reacting the protected ester with a reducing agent to form a protected alcohol;

reacting the protected alcohol with a halogen to form a halogenated compound;

dehalogenating the halogenated compound to form a compound of Formula PPPP having the structure:

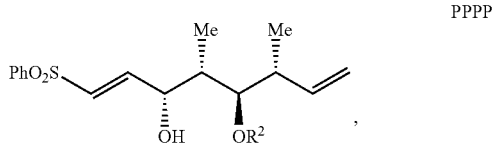

wherein:
Ph is a phenyl group; and
R² is an oxygen protecting group; and reacting the compound of Formula PPPP with methyllithium in the presence of copper to form the compound of Formula V.

Any suitable dialkyl((arylsulfonyl)methyl)phosphonate may be used in a process for preparing a compound of Formula II, III, IV, V, VI, or VII. In some embodiments, in a process for preparing a compound of Formula II, III, IV, V, VI, or VII, the dialkyl((arylsulfonyl)methyl)phosphonate may be dimethyl((phenylsulfonyl)methylphosphonate.

In some embodiments, in a process for preparing a compound of Formula II, III, IV, V, VI, or VII, the alkoxide may be present in an excess of about 2 to about 3 equivalents, such as, for example, in an excess of about 2, 2.1, 2.2, 2.3, 2.4, 2.5, 2.6, 2.7, 2.8, 2.9, or 3 equivalents. Any suitable alkoxide may be used in a process for preparing a compound of Formula II, III, IV, V, VI, or VII. In some embodiments, the alkoxide is a sodium alkoxide, such as, but not limited to, sodium methoxide and sodium ethoxide.

Any suitable polar protic solvent may be used in a process for preparing a compound of Formula II, III, IV, V, VI, or VII. In some embodiments, in a process for preparing a compound of Formula II, III, IV, V, VI, or VII, the polar protic solvent is an alcohol, such as, but not limited to, methanol and ethanol. Any suitable alcohol may be used in a process for preparing a compound of Formula II, III, IV, V, VI, or VII. In some embodiments, the polar protic solvent and alkoxide used in a process for preparing a compound of Formula II, III, IV, V, VI, or VII may be compatible. For example, in some embodiments, the alkoxide may be sodium methoxide and the polar protic solvent may be methanol.

According to some embodiments of the present invention, a method of using a compound of Formula II', III', IV', V', VI', and/or VII' is provided. In some embodiments, a method of using a compound of Formula II, I, IV, V, VI, and/or VII is provided.

In some embodiments, a compound of Formula II', III', IV', V', VI', and/or VII' may be used to prepare a natural product or an intermediate thereof. In some embodiments, a compound of Formula II, III, IV, V, VI, and/or VII may be used to prepare a natural product or an intermediate thereof. Exemplary natural products include, but are not limited to, spirangien A, spirangien B, dolabriferol, scytophycin C, zincophorin, stigmatellin, rifamycin SV, tirandamycin A, aplyronine A, aplyronine E, reidispongioloide, misakinolide, and/or mycarolide. FIG. 1 illustrates exemplary natural products and indicates areas (i.e., the boxed areas) that are consistent with a compound of Formula II or IV and/or in which a compound of Formula II or IV may be used to prepare that portion of the natural product Thus, a compound of Formula II or IV may be used to prepare the shown natural products or intermediates thereof.

In some embodiments, a compound described herein, or a salt thereof, may be useful in a method of synthesizing a fused aminodihydrothiazine derivative. In some embodiments, the compound may be a compound of Formula II', II, III', III, IV', IV, V', V, VI, VI, VII', and/or VII.

In some embodiments, a compound described herein, or salt thereof, may be used to prepare a combinatorial library. In some embodiments, a compound of Formula II', III', IV', V', VI', and/or VII' may be used to prepare a combinatorial library. In some embodiments, a compound of Formula II, III, IV, V, VI, and/or VII may be used to prepare a combinatorial library.

In order that the invention described herein may be more fully understood, the following examples are set forth. It should be understood that these examples are for illustrative purposes only and are not to be construed as limiting this invention in any manner.

EXAMPLES

General:

Column chromatography was carried out using Biotage SP4. Solvent removal was carried out using either a Btlchii rotary evaporator or a Genevac centrifugal evaporator. Preparative LC/MS was conducted using a Waters autopurifier and 19×100 mm XTerra 5 micron MS C18 column under acidic mobile phase condition. NMR spectra were recorded using Varian 400 MHz spectrometer.

When the term "inerted" is used to describe a reactor (e.g., a reaction vessel, flask, glass reactor, and the like) it is meant that the air in the reactor has been replaced with an essentially moisture-free or dry, inert gas (such as nitrogen, argon, and the like). The term "equivalent" (abbreviation: eq) as used herein describes the stoichiometry (molar ratio) of a reagent or a reacting compound by comparison to a pre-established starting material. The term "weight" (abbreviation: wt) as used herein corresponds to the ratio of the mass of a substance or a group of substances by comparison to the mass of a particular chemical component of a reaction or purification specifically referenced in the examples below. The ratio is calculated as: g/g, or Kg/Kg. The term "volume" (abbreviation: vol) as used herein corresponds to the ratio of the volume of a given substance or a group of substances to the mass or volume of a pre-established chemical component of a reaction or purification. The units used in the equation involve matching orders of magnitude. For example, a ratio is calculated as: mL/mL, mL/g, L/L or L/Kg.

General methods and experimentals for preparing compounds of the present invention are set forth below. In certain cases, a particular compound is described by way of example. However, it will be appreciated that in each case a series of compounds of the present invention were prepared in accordance with the schemes and experimentals described below.

The following abbreviations are used herein:

| Abbreviation | Definition |
| --- | --- |
| TMS | Trimethylsilyl |
| TBAF | Tetrabutylammonium fluoride |
| NaOH | Sodium hydroxide |
| Bu$_4$N HSO$_4$ | Tetrabutylammonium hydrogen sulfate |
| THF | Tetrahydrofuran |
| rt | Room temperature |
| h | Hour(s) |
| NaCl | Sodium chloride |
| HCOOH | Formic acid |
| V | Volumes |
| wt | Weights |
| CDI | 1,1'-Carbonyldiimidazole |
| DCM | Dichloromethane |
| Aq | Aqueous |
| Sat. | Saturated |
| HCl | Hydrochloric acid |
| HRMS | High Resolution Mass Spectrometry |
| nBuLi | n-butyl lithium |
| NH$_4$Cl | Ammonium chloride |
| MeOH | Methanol |
| EtOAc | Ethyl acetate |
| NaHCO$_3$ | Sodium bicarbonate |
| M | Molar (moles/liter) |
| T | Temperature |
| MTBE | Methyl tert-butyl ether |
| TLC | Thin layer chromatography |
| N | Normal (equivalents per liter) |
| iPrMgBr | Isopropyl magnesium bromide |
| LiCl | Lithium chloride |
| NaOAc | Sodium acetate |
| NH$_4$OH | Ammonium hydroxide |
| HPLC | High performance liquid chromatography |
| ee | Enantiomeric excess |
| DMI | 1,3-Dimethyl-2-imidazolidinone |
| UV | Ultraviolet |
| RRT | Relative retention time |
| OROT | Optical rotation |
| Bz | Benzoyl |
| T3P ® (Archimica) | n-propyl phosphonic acid anhydride |
| Ph | Phenyl |
| TES | Triethylsilyl |

A. Preparation of Compounds of Formula 1

Compounds of Formulas 1a and 1b were prepared as shown in Scheme 1.

Scheme 1:
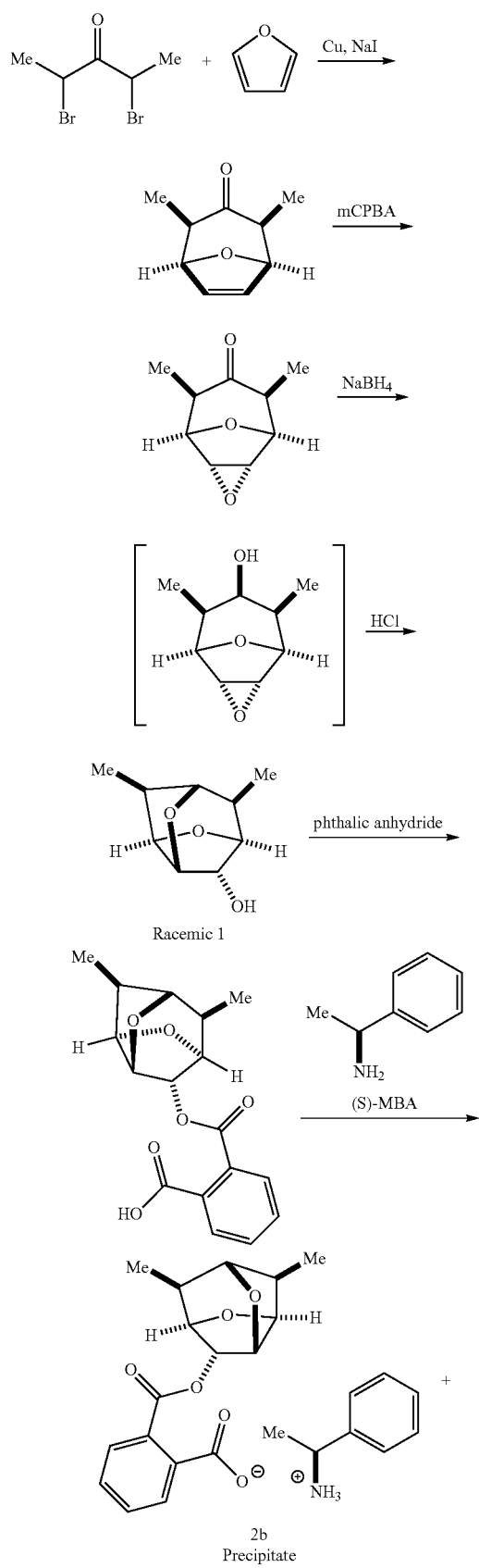
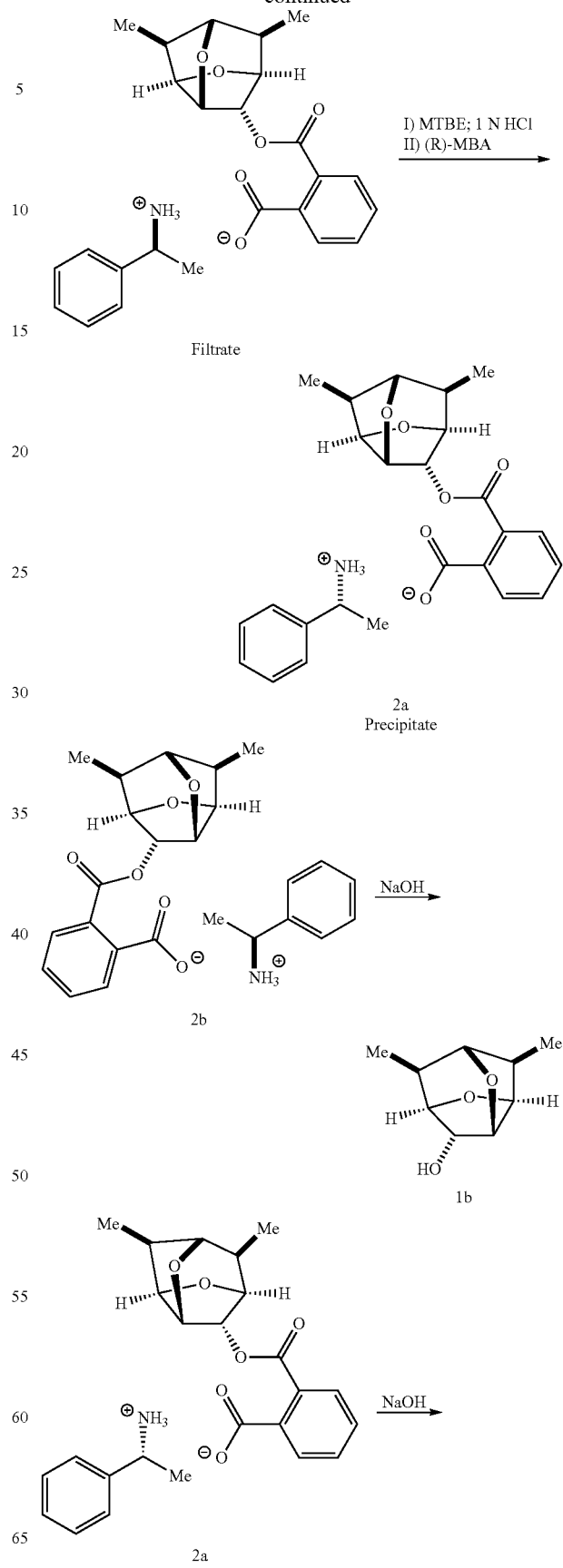

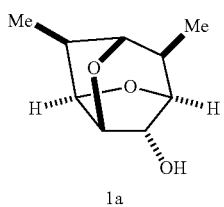

1a

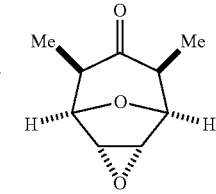

(1R,2R,4S,5S,6S,8R)-6,8-dimethyl-3,9-dioxatricyclo [3.3.1.0²,⁴]nonan-7-one

Synthesis and Resolution of Alcohols of Formulas 1a and 1b.

To a stirred solution of (1R,2S,4R,5S)-2,4-dimethyl-8-oxabicyclo[3.2.1]oct-6-en-3-one (1.06 kg) in 1,2-dichloroethane (10 L) at room temperature was added m-chloroperbenzoic acid (1.80 kg) in one portion. The resulting suspension was stirred under reflux (at 70-75° C.) for 5 h. More m-chloroperbenzoic acid (180 g) was added and stirring was continued for additional 3 h. The mixture was cooled to 0° C. and stirred at 0° C. overnight. The resulting precipitate was filtered and washed with methylene chloride (4 L). The filtrate was sequentially washed with 10 M sodium carbonate in water (7 L) and water (4 L). The organic layer was concentrated in vacuo and chased twice with n-heptane (2 L). The resulting pale yellow solid was dissolved in MTBE (2.5 L) by heating to 55° C., treated with n-heptane (0.8 L), and stood at −20° C. for 3 days. The precipitate was collected by vacuum filtration and washed with a 3:2 mixture of MTBE and n-heptane (750 mL) to give the title compound (1050 g, 90%) as a white solid. ¹H NMR (CDCl₃, 400 MHz): δ 4.40 (t, 2H), 3.55 (t, 2H), 2.80 (m, 2H), 1.05 (d, 6H).

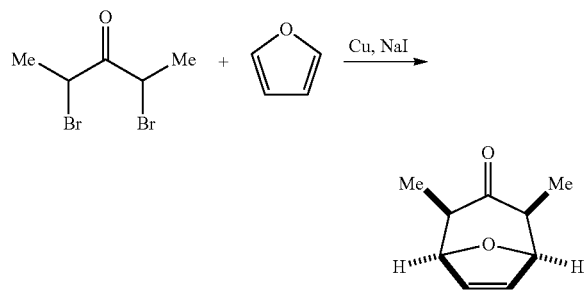

(1R,2S,4R,5S)-2,4-Dimethyl-8-oxabicyclo[3.2.1]oct-6-en-3-one

To a 22 L reactor under nitrogen were charged acetonitrile (6.2 L) and sodium iodide (4420 g) at room temperature. While vigorously stirring, the suspension was treated with copper (969 g) and freshly distilled furan (1.47 L). Then, a solution of 2,4-dibromo-3-pentanone (1247 g) in acetonitrile (1.2 L) was added maintaining the internal temperature below 55° C. The resulting mixture was stirred at 45-50° C. for 4 h. After cooling to 20° C., the reaction was quenched with water (4 L) and MTBE (4 L), and the resulting mixture was stirred at 0° C. overnight. The resulting precipitate was filtered through celite 545 (2.4 kg) and sequentially washed with MTBE (1 L) and methylene chloride (4 L). The organic layer was separated from the filtrate, diluted with MTBE (1 L), and sequentially washed with 28% ammonium hydroxide (3.5 L) and a mixture of 28% ammonium hydroxide (3 L) and water (1 L). The organic layer was further diluted with MTBE (6.5 L), and sequentially washed with water (2 L, containing sodium chloride (25 g)), a mixture of 28% ammonium hydroxide (1.5 L) and water (1 L), and water (4 L). The first aqueous layer was back-extracted twice with a mixture of MTBE (3 L) and methylene chloride (3 L). The organic layers were combined, washed twice with a mixture of 28% ammonium hydroxide (2.5 L), water (1 L) and sodium chloride (25 g), and then washed with water (4 L). The yellow organic layer was concentrated under reduced pressure, and azeotroped with n-heptane (4 L). The residue was treated with n-heptane (4 L), concentrated down to ~3 L, and stirred at −20° C. overnight. The resulting faint yellow solid was collected by vacuum filtration, washed with cold heptane (500 mL), and dried under vacuum overnight at room temperature to give the title compound (549 g, 71%). ¹H NMR (CDCl₃, 400 MHz): δ 6.35 (s, 2H), 4.85 (d, 2H), 2.8 (m, 2H), 0.95 (d, 6H).

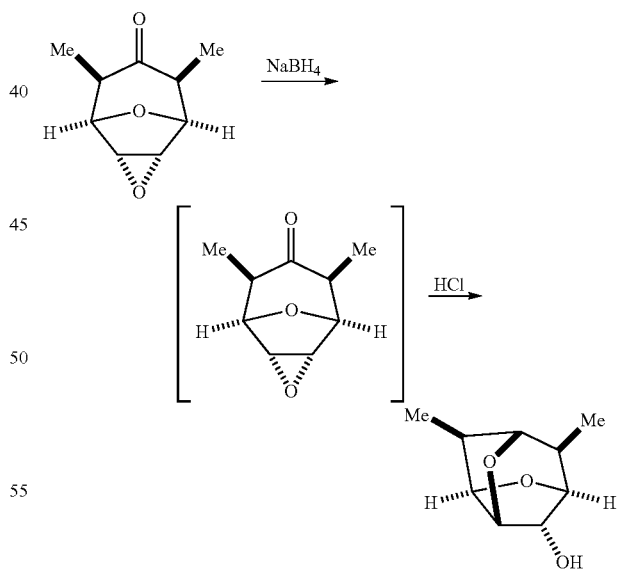

Synthesis of rac-6,7-dimethylhexahydro-2,5-methanofuro[3,2-b]furan-3-ol

To a cold (−15° C.) suspension of sodium borohydride (337 g) in methanol (4 L) in a 22 L reactor under nitrogen was carefully charged a solution of (1R,2R,4S,5S,6S,8R)-6,8-dimethyl-3,9-dioxatricyclo[3.3.1.0²,⁴]nonan-7-one (1 kg) in a mixture of methanol (2 L) and methylene chloride (4 L) over 1.5 h maintaining the internal temperature below 0° C. The resulting mixture was stirred at −5-0° C. for 2 h. After quenching the reaction with water (160 mL), the mixture was concentrated under vacuum and chased with methylene chloride (2 L). The resulting solid was dissolved in methylene chloride (8 L) and washed with water (4 L). The aqueous layer was back-extracted with methylene chloride (4 L). The organic layers were combined, dried over anhydrous sodium sulfate and stood at 0° C. overnight. The sodium sulfate was removed by vacuum filtration and rinsed with methylene chloride (1 L).

The filtrate was treated with 5.5 M HCl in isopropyl alcohol (3 L) at 5° C. and stirred at 20-30° C. for 1 h. The reaction mixture was concentrated under vacuum at 30° C. and chased twice with toluene (2 L) to give the title compound (975 g, 96%) as a pale yellow solid. $^1$H NMR (C$_6$D$_6$, 400 MHz): 4.30 (t, 1H), 4.10 (t, 1H), 4.00 (t, 1H), 3.75 (t, 1H), 3.15 (t, 1H), 2.45 (s, 1H), 1.85 (m, 1H), 1.45 (m, 1H), 0.60 (d, 3H), 0.55 (d, 3H).

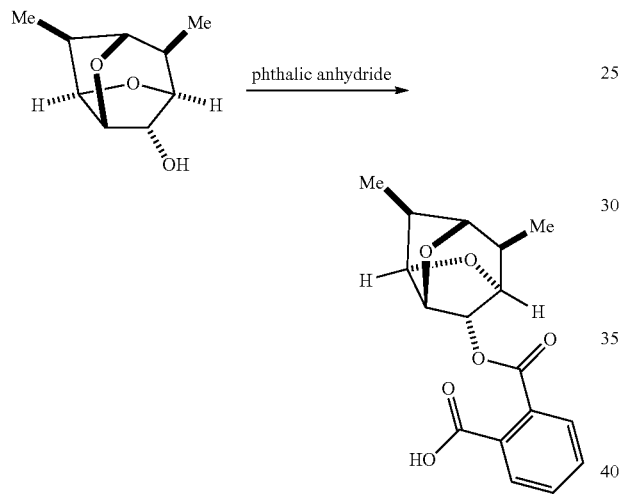

Synthesis of the Corresponding Phthalate of the Racemic Alcohol rac-6,7-Dimethylhexahydro-2,5-methanofuro[3,2-b]furan-3-ol (970 g) was dissolved in a mixture of triethylamine (1.99 L) and toluene (2.1 L), treated with phthalic anhydride (925 g), and stirred at 70° C. for 2 h. The mixture was cooled to 10° C. and treated with 3 M hydrogen chloride in water (7 L) maintaining the temperature below 30° C. White solids began falling out of solution. The mixture was stirred at rt for an additional 20 min. The white solid product was then collected by vacuum filtration, washed with water (2 L), and dried under vacuum. The crude product was chased with toluene (4 L) and then heated in toluene (5.6 L) to 70° C. to obtain a clear solution. The solution was allowed to cool to 65° C. where solids began falling out of solution, and slowly cooled to rt overnight. The white solid product was collected by vacuum filtration, washed with toluene (1 L), and dried under vacuum. The product was recrystallized again in toluene (5.6 L) by heating to 75°, cooling to rt at a rate of 10° C. per hour, and stirring at rt overnight. Solids began falling out of solution at 65° C. The resulting precipitate was collected by vacuum filtration, washed with toluene (1 L), and dried under vacuum at 40° C. to give the title compound (1.65 kg, 91%) as a white solid. $^1$H NMR analysis showed that there was 4% of the suspected equatorial by-product and approximately 4% of triethylamine salt present. $^1$H NMR (CDCl$_3$, 400 MHz): 7.80 (d, 1H), 7.65 (d, 1H), 7.55 (m, 2H), 5.50 (s, 1H), 4.80 (t, 1H), 4.50 (t, 1H), 4.35 (t, 1H), 3.75 (t, 1H), 3.10 (m, 1H), 2.00 (m, 1H), 1.05 (d, 3H), 0.85 (d, 3H).

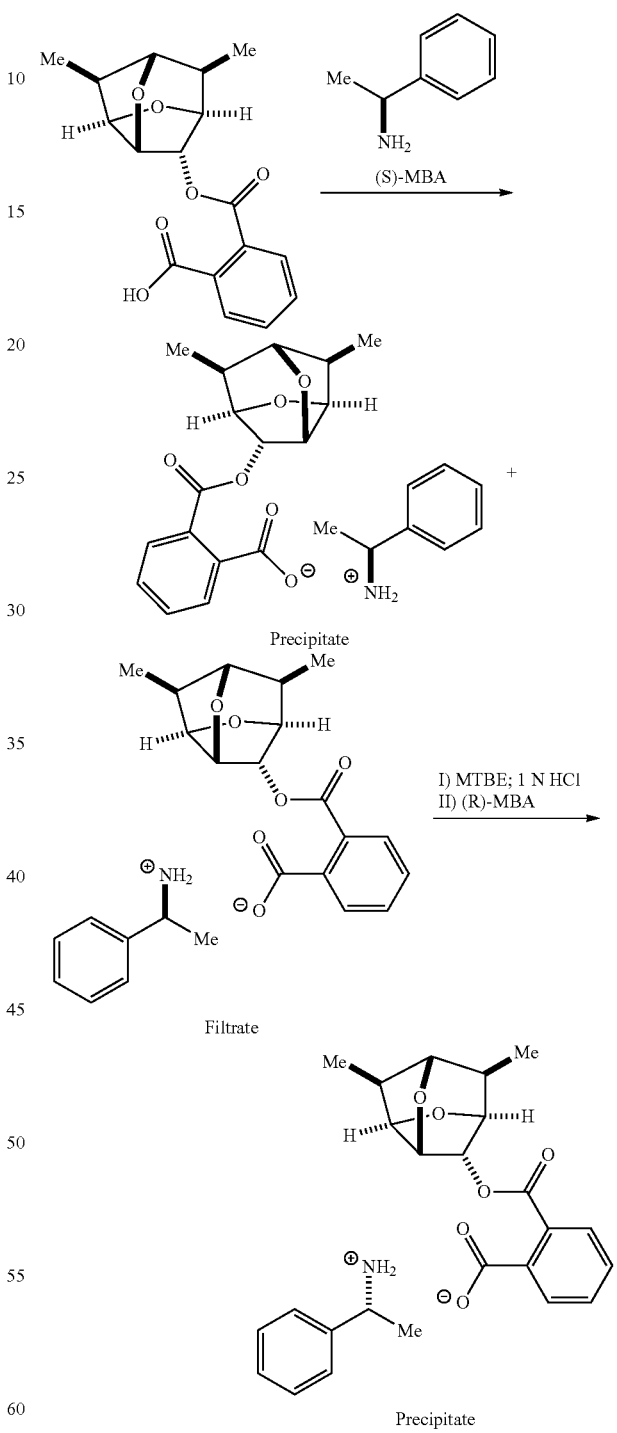

Resolution of the Phthalate with α-methylbenzylamine:

A phthalate of rac-6,7-dimethylhexahydro-2,5-methano-furo[3,2-b]furan-3-ol (800 g) was dissolved in acetone (12 L) with slight heating to 50° C. The resulting clear solution was treated with (S)-methylbenzylamine (324 mL) and stirred at 50° C. for 10 min. The mixture was stirred at 45° C. for 1 h, at 40° C. for 1 h, and at 35° C. for 1 h before cooling to 18-22° C. over 2 h. The mixture was then allowed to stir at 18-22° C. for 17 h. The solid precipitate was collected by vacuum filtration, washed with acetone (1 L), and dried under vacuum at 30° C. to give (S)-1-phenylethanaminium 2-((((2R,3R,3aR,5S,6R,6aS,7S)-6,7-dimethyl hexahydro-2,5-methanofuro[3,2-b]furan-3-yl)oxy)carbonyl)benzoate (372 g, 36.6%, dr=98.4:1.6 by chiral HPLC) as a white solid. $^1$H NMR (CDCl$_3$, 400 MHz): δ 8.1 (bs, 3H), 7.60 (d, 1H), 7.55 (d, 1H), 7.30-7.40 (m, 4H), 7.20 (m, 3H), 5.30 (s, 1H), 4.60 (t, 1H), 4.30 (t, 1H), 4.25 (t, 1H), 3.95 (t, 1H), 3.65 (t, 1H), 2.10 (m, 1H), 1.85 (m, 1H), 1.70 (d, 3H), 0.95 (d, 3H), 0.75 (d, 3H).

The filtrate was concentrated under vacuum and then dissolved in MTBE (4 L). The solution was then washed with 1.0 M aqueous HCl (3 L) and the aqueous layer was back extracted with MTBE (2 L). The organic layers were combined, washed with water (2 L), and concentrated under vacuum at 30° C. to give a red-brown foam. The foam was chase with MTBE (2 L) and then with acetone (2 L). The brown foam (520 g) was dissolved in acetone (7.8 L) at 50° C. and treated with (R)-α-methylbenzylamine (210 mL). The mixture was stirred at 50° C. for 10 min, at 45° C. for 1 h, at 40° C. for 1 h, and at 35 for 1 h before cooling to 18-22° C. over 2 h. The mixture was then allowed to stir at 18-22° C. over 17 h. The precipitate was collected by vacuum filtration, washed with acetone (0.5 L), and dried under vacuum at 35° C. to give (R)-1-phenylethanaminium 2-((((2S,3S3aS,5R,6S,6aR,7R)-6,7-dimethylhexahydro-2,5-methanofuro[3,2-b]furan-3-yl)oxy)carbonyl)benzoate (402 g, 40%, dr=96.7:3.3 by chiral HPLC) as a white solid. $^1$H NMR (CDCl$_3$, 400 MHz): δ 8.1 (bs, 3H), 7.60 (d, 1H), 7.55 (d, 1H), 7.30-7.40 (m, 4H), 7.20 (m, 3H), 5.30 (s, 1H), 4.60 (t, 1H), 4.30 (t, 1H), 4.25 (t, 1H), 3.95 (t, 1H), 3.65 (t, 1H), 2.10 (m, 1H), 1.85 (m, 1H), 1.70 (d, 3H), 0.95 (d, 3H), 0.75 (d, 3H).

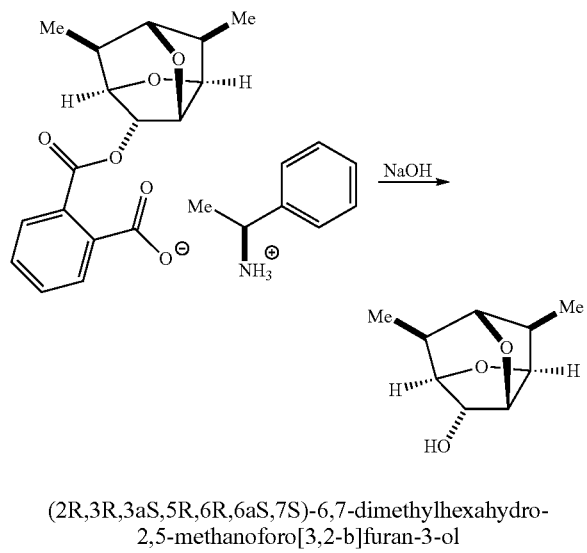

(2R,3R,3aS,5R,6R,6aS,7S)-6,7-dimethylhexahydro-2,5-methanoforo[3,2-b]furan-3-ol (S)-1-phenylethanaminium 2-((((2R,3R,3aR,5S,6R,6aS,7S)-6,7-dimethylhexahydro-2,5-methanofuro[3,2-b]furan-3-yl)oxy)carbonyl)benzoate (362 g) was dissolved in 1.0 M aqueous HCl (1.7 L) and MTBE (2 L). The organic layer was separated and the aqueous layer was extracted with MTBE (1 L). The organic layers were combined, washed with 1.0 M aqueous HCl (0.4 L), and treated with a solution of sodium hydroxide (99 g) in water (1 L). After stirring at rt for 1 h, the organic layer was separated and the aqueous layer was extracted with MTBE (1 L×2) and ethyl acetate (0.5 L). The combined organic layers were concentrated under vacuum to give the title compound (127 g, 91%) as a white solid. $^1$H NMR (CDCl$_3$, 400 MHz): δ 4.50 (t, 1H), 4.40 (t, 1H), 4.20 (t, 1H), 4.00 (t, 1H), 3.70 (s, 1H), 2.30 (m, 1H), 2.20 (m, 1H), 2.00 (m, 1H), 1.00 (d, 3H), 0.90 (d, 3H).

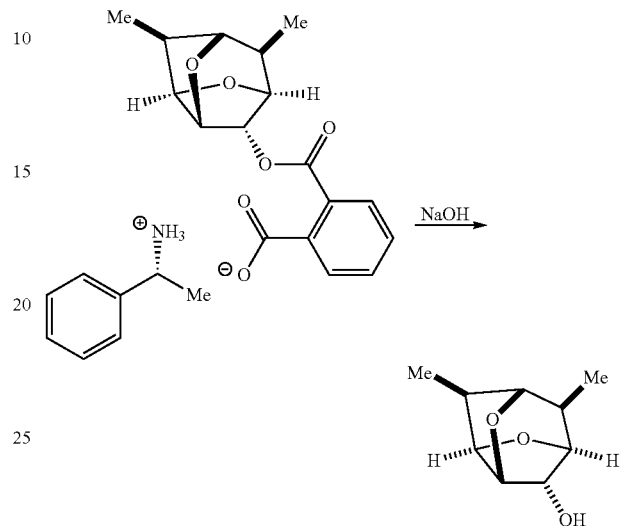

(2S,3S,3aR,5S,6S,6aR,7R)-6,7-dimethylhexahydro-2,5-methanofuro[3,2-b]furan-3-ol (R)-t-phenylethanaminium 2-((((2S,3S,3aS,5R,6S,6aR,7R)-6,7-dimethylhexahydro-2,5-methanofuro[3,2-b]furan-3-yl)oxy)carbonyl)benzoate (397 g) was dissolved in a mixture of 1.0 M aqueous HCl (1.9 L) and MTBE (2 L). The organic layer was separated and the aqueous layer was extracted with MTBE (1 L). The organic layers were combined, washed with 1.0 M aqueous HCl (0.5 L), and then treated with a solution of sodium hydroxide (108 g) in water (1 L). After stirring at rt for 1 h, the organic layer was separated and the aqueous layer was extracted with MTBE (1 L×2) and ethyl acetate (0.5 L). The combined organic layers were concentrated under vacuum to give the title compound (135.8 g, 88%) as a white solid. $^1$H NMR (CDCl$_3$, 400 MHz): δ 4.40 (t, 1H), 4.30 (t, 1H), 4.20 (t, 1H), 4.00 (t, 1H), 3.70 (s, 1H), 2.30 (m, 2H), 2.00 (m, 1H), 1.00 (d, 3H), 0.90 (d, 3H).

B. Stereochemistry Determination for Compounds of Formula 1.

The stereochemistry of compounds of Formula 1 was determined using Mosher ester reacations as described below.

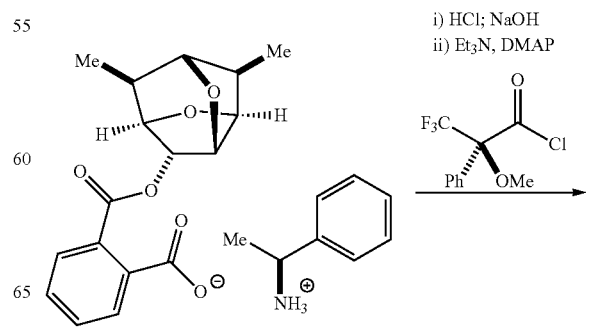

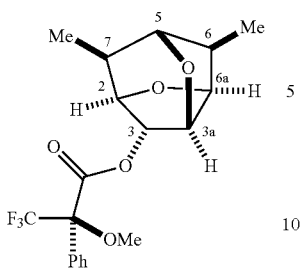

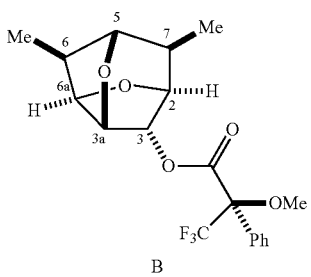

B

Mosher ester of (2R,3R,3aS,5R,6R,6aS,7S)-6,7-dimethylhexahydro-2,5-methanofuro[3,2-b]furan-3-ol (S)-1-1-phenylethanaminium 2-((((2R,3R,3aR,5S,6R,6aS,7S)-6,7-dimethylhexahydro-2,5-methanofuro[3,2-b]furan-3-yl)oxy)carbonyl)benzoate (105 mg, 0.24 mmol) was suspended in MTBE (6 mL) and washed twice with 1 N aqueous HCl (1 mL). The organic layer was treated with 3 N NaOH (1 mL) and stirred at rt for 1 h. The organic layer was separated, dried over MgSO$_4$ and concentrated in vacuo to give a crude alcohol.

Ca. 5 mg of the crude alcohol was dissolved in CH$_2$Cl$_2$ (0.3 mL) and treated with triethylamine (30 uL), (S)-methoxy-trifluoromethylphenylacetyl chloride (18 mg) and a catalytic amount of DMAP. After stirring at rt for 30 min, the mixture was diluted with water (5 mL) and MTBE (5 mL). The organic layer was separated, filtered through silica gel pad, and concentrated in vacuo to give a crude Mosher ester, which was analyzed by NMR. $^1$H NMR (CDCl$_3$, 400 MHz): δ 7.58 (m, 2H, Ph), 7.42 (m, 3H, Ph), 5.37 (s, 1H, C3-H), 4.72 (m, 1H, C3a-H), 4.42 (m, 1H, C6a-H), 4.30 (m, 1H, C2-H), 3.80 (s, lit, C5-H), 3.55 (s, 3H, OMe), 2.35 (q, 1H, C6-H), 2.07 (m, 1H, C7-H), 1.12 (d, 3H, Me), 0.89 (d, 3H, Me).

Mosher Ester of a Racemic Alcohol:

The phthalate of racemic alcohol (77 mg) prepared by above procedure was dissolved in MTBE (6 mL) and treated with 3 N NaOH (1 mL). After stirring at rt for 1 h, the organic layer was separated, dried over MgSO4 and concentrated in vacuo.

Ca. 5 mg of the crude alcohol was dissolved in CH$_2$Cl$_2$ (0.3 mL) and treated with triethylamine (30 uL), (S)-methoxy-trifluoromethylphenylacetyl chloride (18 mg) and a catalytic amount of DMAP. After stirring at rt for 30 min, the mixture was diluted with water (5 mL) and MTBE (5 mL). The organic layer was separated, filtered through silica gel pad, and concentrated in vacuo to give a crude Mosher ester, which was analyzed by NMR. Peaks corresponding to the compound A and B was assigned based on literature (Rieser, M. J. et al., *J. Am. Chem. Soc.* 1992, 114, 10203). $^1$H NMR (CDCl$_3$, 400 MHz): δ 7.58 (m, 4H, Ph), 7.42 (m, 6H, Ph), 5.37 (s, 2H, C3-H for A and B), 4.72 (m, 1H, C3a-H for A), 4.62 (m, 1H, C3a-H for B), 4.42 (m, 2H, C5a-H for A and B), 4.38 (m, 1H, C2-H for B), 4.30 (m, 1H, C2-H for A), 3.80 (s, 2H, C5-H for A and B), 3.60 (s, 3H, OMe for B), 3.55 (s, 3H, OMe for A), 2.35 (m, 2H, C6-H for A and B), 2.07 (m, 2H, C.7-H for A and B), 1.12 (d, 3H), 1.10 (d, 3H), 0.89 (2d, 6H).

C. Oxidation of Alcohols of Formulas 1a and 1b to Lactones of Formulas Ia and Ib, Respectively.

Compounds of Formulas Ia and Ib were prepared as shown in Scheme 2 and described below.

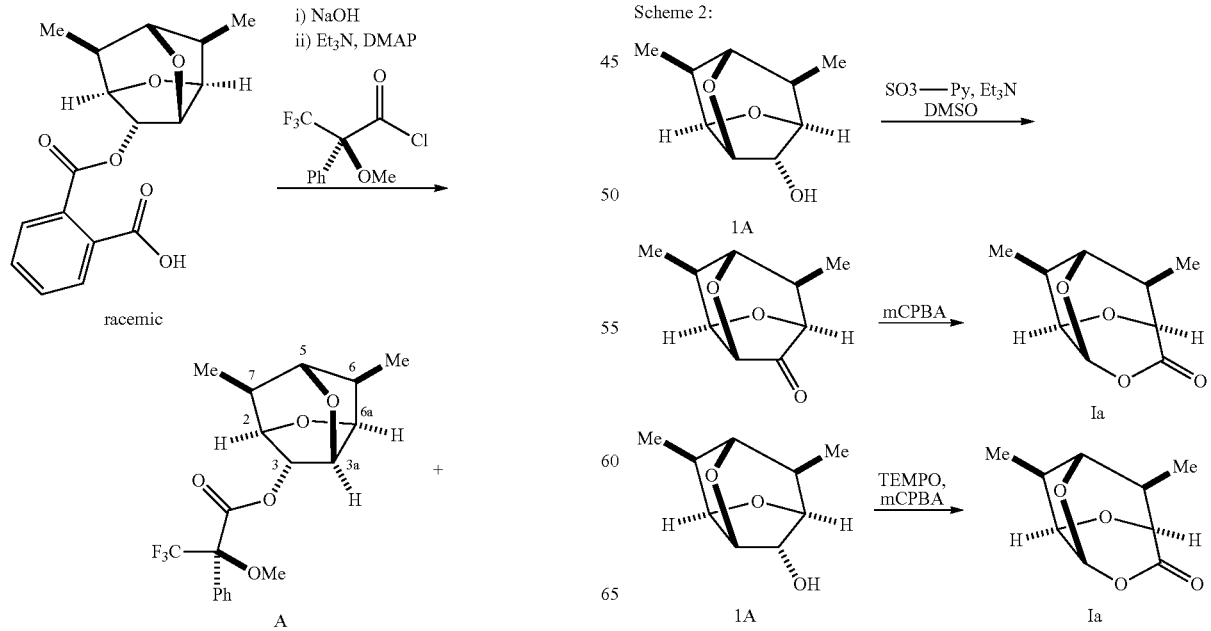

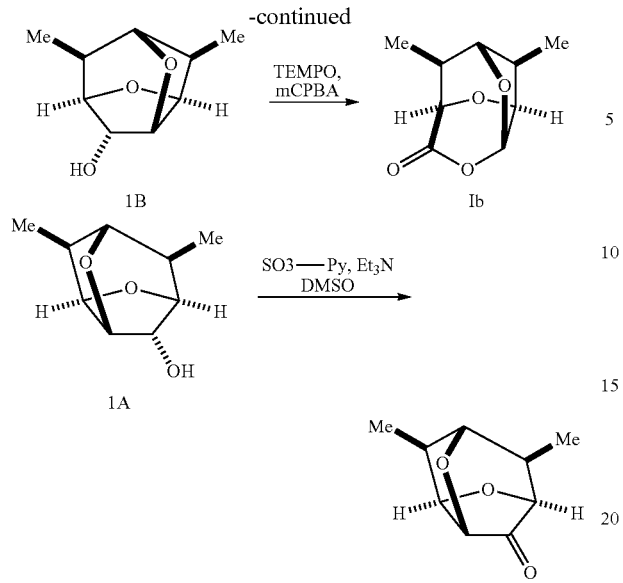

1B

1A

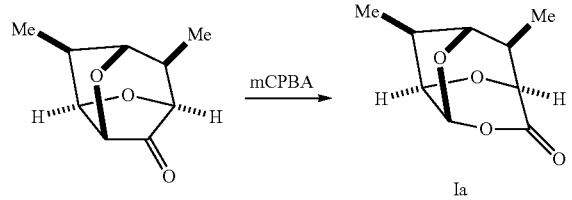

Ia (2S,4aR,6R,7S,7aR,8R)-7,8-dimethyltetrahydro-2,6-methanofuro[2,3-b][1,4]dioxin-3(2H)-one (2S,3aS,5R,6S,6aR,7R)-6,7-dimethyltetrahydro-2,5-methanofuro[3,2-b]furan-3(2H)-one Sulfur trioxide-pyridine complex (118 g, 741 mmol) was dissolved in DMSO (400 mL) and stirred at ambient temperature for 20 min. After cooling to 0° C., the mixture was treated with a mixture of (2S,3S,3aR,5S,6S,6aR,7R)-6,7-dimethylhexahydro-2,5-methanofuro[3,2-b]furan-3-ol (42.2 g, 248 mmol) and triethylamine (207 mL, 1.49 mol) in methylene chloride (400 mL) over 1 h maintaining the internal temperature below 10° C. After stirring at ambient temperature for 4 h, the reaction was quenched with water (400 mL). The organic layer was separated and the aqueous layer was extracted with MTBE (500 mL). The organic layers were combined, washed twice with water (200 mL) and then with brine (150 mL), and concentrated in vacuo.

The residue was dissolved in MTBE (50 mL) and treated with n-heptane (200 mL). The resulting turbid solution was stirred at ambient temperature for 18 h. The precipitate was filtered, washed with n-heptane (20 mL), and dried under nitrogen purge to give the title compound (1$^{st}$ crop, 5.4 g, 13%). The filtrate was concentrated in vacuo and dissolved in a mixture of MTBE (2 mL) and n-heptane (55 mL) with heating. The resulting clear solution was stirred at ambient temperature for 1 h and at 0° C. for 3 h. The precipitate was filtered and washed with n-heptane to give the 2$^{nd}$ crop (13.8 g, 33%). $^1$H NMR (CDCl$_3$, 400 MHz): δ 4.68 (m, 1H), 4.29 (m, 1H), 3.96 (s, 1H), 3.90 (m, 1H), 2.48 (q, 1H), 2.36 (m, 1H), 1.10 (d, 3H), 0.93 d, 3H).

(2S,3aS,5R,6S,6aR,7R)-6,7-dimethyltetrahydro-2,5-methanofuro[3,2-b]furan-3(2H)-one (7.07 g, 45.8 mmol) was dissolved in methylene chloride (120 mL) and treated with m-chloroperbenzoic acid (14.1 g, 81.7 mmol). After stirring at rt for 18 h, the mixture was diluted with MTBE (150 mL) and washed with 1 N aqueous NaOH solution (50 mL) and brine (30 mL). The organic layer was separated, dried over MgSO$_4$ and concentrated in vacuo. The residue was further purified by crystallization with MTBE and n-heptane to give the title compound (total 5.9 g, 62.7%). $^1$H NMR (CDCl$_3$, 400 MHz): δ 5.95 (t, 1H), 4.35 (t, 1H), 4.20 (t, 1H), 3.95 (t, 1H), 2.40 (m, 1H), 2.10 (m, 1H), 1.00 (d, 3H), 0.95 (d, 3H).

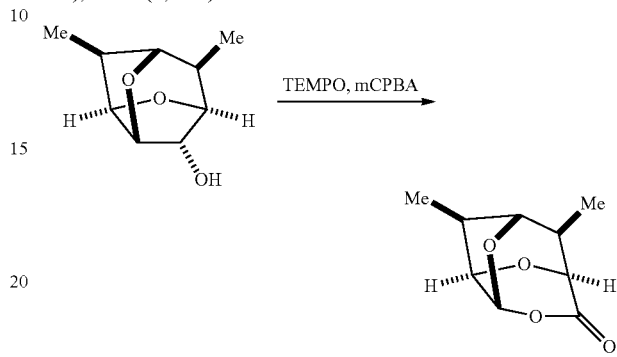

(2S,4aR,6R,7S,7aR,8R)-7,8-dimethyltetrahydro-2,6-methanofuro[2,3-b][1,4]dioxin-3(2H)-one (2S,3S,3aR,5S,6S,6aR,7R)-6,7-dimethylhexahydro-2,5-methanofuro[3,2-b]furan-3-ol (20 g) was dissolved in a mixture of methylene chloride (300 mL) and saturated aqueous NaHCO$_3$ (230 mL). After cooling to 0° C., the mixture was treated with 2,2,6,6-tetramethyl-1-piperidinyloxy, free radical (370 mg) and m-chloroperbenzoic acid (105 g). The mixture was stirred at 0° C. for 10 min and at rt for 16 h. After dilution with MTBE (400 mL), the organic layer was separated, and sequentially washed with a solution of sodium bisulfite (37 g) in water (100 mL), saturated aqueous NaHCO$_3$ (150 mL×3), and water (100 mL). The organic layer was concentrated under vacuum at 30° C. and chased with MTBE (100 mL) to furnish a yellow-white solid. The crude product was recrystallized from isopropyl alcohol (65 mL) by heating to 55° C., slowly cooling to rt over 4 h, and stirring at 0° C. for 1 h. The precipitate was collected by vacuum filtration, washed with isopropyl alcohol (15 mL), and dried under vacuum to give the title compound (16.5 g, 76%) as a white solid. $[α]_D^{20}$=+269.7° (c 0.51, MeOH); $^1$H NMR (CDCl$_3$, 400 MHz): δ 5.95 (t, 1H), 4.35 (t, 1H), 4.20 (t, 1H), 3.95 (t, 1H), 2.40 (m, 1H), 2.10 (m, 1H), 1.00 (d, 3H), 0.95 (d, 3H).

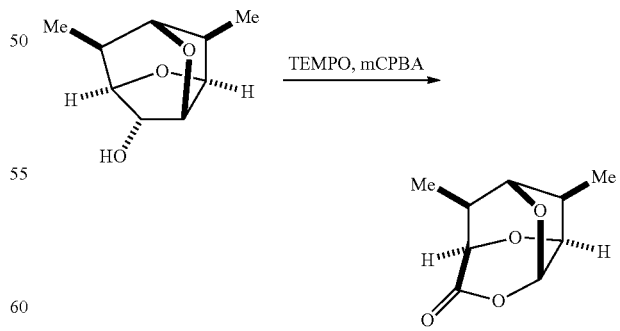

(2R,4aS,6S,7R,7aS,8S)-7,8-dimethyltetrahydro-2,6-methanofuro[2,3-b][1,4]dioxin-3(2H)-one (2R,3R,3aS,5R,6R,6aS,7S)-6,7-dimethylhexahydro-2,5-methanofuro[3,2-b]furan-3-ol (100 g) was dissolved in a mixture of methylene chloride (1.5 L) and saturated aqueous NaHCO$_3$ (1.15 L). After cooling to 10° C., the mixture was treated with 2,2,6,6-tetramethyl-1-piperidinyloxy, free radical (1.8 g) and m-chloroperbenzoic acid (530 g). The mixture was stirred at 10° C. for 30 min and at rt overnight. After dilution with MTBE (2 L), the organic layer was separated, and sequentially washed with a solution of sodium bisulfite (167 g) in water (1 L), saturated aqueous NaHCO$_3$ (1 L×3), and water (500 mL). The organic solution was then concentrated under vacuum and chased with toluene (1 L). The resulting solid was suspended in toluene (350 mL), heated to 45° C. and then allowed to cool to rt overnight. The white solid precipitate (mCPBA residue) was collected by vacuum filtration and washed with toluene (50 mL). The filtrate was concentrated under vacuum and recrystallized from isopropyl alcohol (300 mL) by dissolving at 55° C., slowly cooling to 22° C. over 1.5 h, and stirring at 0-5° C. for 1 h. The precipitate was collected by vacuum filtration, washed with isopropyl alcohol (75 mL), and dried under vacuum at 35° C. to give the title compound (85.5 g, 79%) as a white solid. $[\alpha]_D$=−248.6° (c 0.52, MeOH); $^1$H NMR (CDCl$_3$, 400 MHz): δ 5.95 (t, 1H), 4.40 (t, 1H), 4.20 (t, 1H), 4.00 (t, 1H), 2.40 (m, 1H), 2.20 (m, 1H), 1.05 (d, 3H), 1.00 (d, 3H).

D. Elaboration of Lactone of Formula a to Protected Tetrad 3

A compound of Formula Ia was elaborated as shown in Scheme 3 and described below.

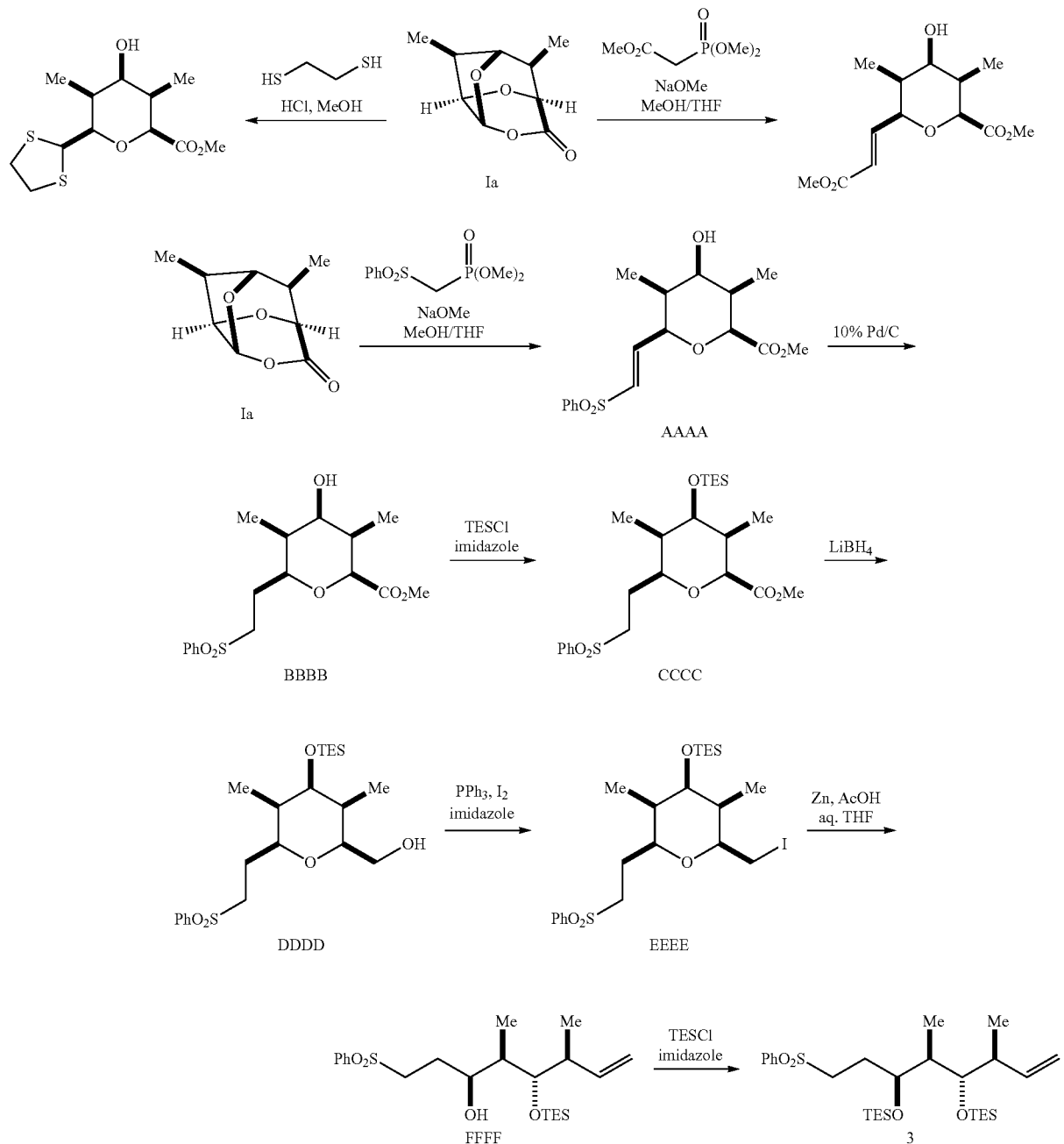

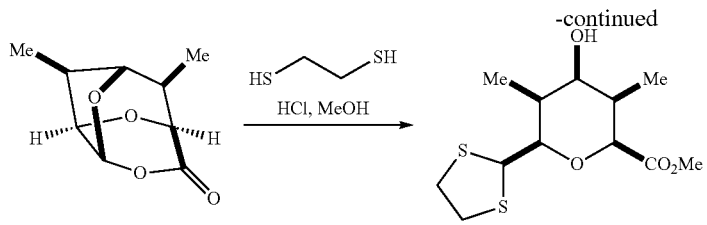

Methyl 6 (1,3-dithiolan-2-yl)-4-hydroxy-3,5-dimethyltetrahydro-2H-pyran-2-carboxylate 7,8-dimethyltetrahydro-2,6-methanofuro[2,3-b][1,4]dioxin-3(2H)-one (20 mg, 0.11 mmol) was dissolved in 4 M hydrogen chloride in 1,4-dioxane (0.5 mL, 18 equiv) and treated with methanol (0.044 mL) and 1,2-ethanedithiol (0.020 mL, 2 equiv). After stirring at rt for 3 days, the reaction was quenched with sat. NaHCO3. The mixture was extracted with MTBE. The organic layer was washed with brine and concentrated in vacuo. The crude product was purified by column chromatography (ethyl acetate/n-heptane=1/10 to 1/3) to give the title compound (3 mg, 9%) as a white solid. $^1$H NMR (CDCl$_3$, 400 MHz): δ 4.70 (d, 1H), 4.16 (dd, 1H), 4.04 (t, 1H), 3.82 (s, 3H), 3.33 (dd, 1H), 3.20-3.28 (m, 4H), 2.26 (m, 2H), 1.06 (d, 3H), 0.96 (d, 3H).

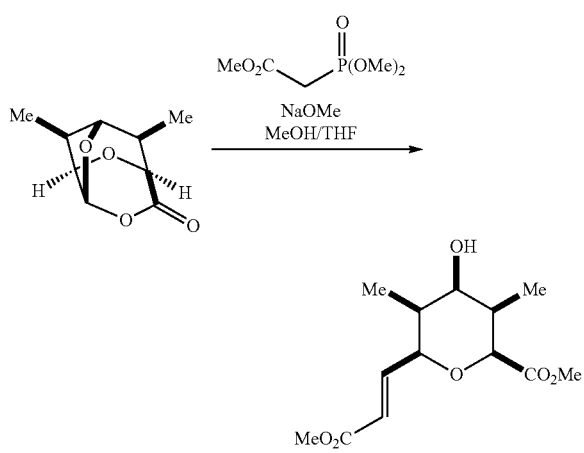

(2S,3R,4R,5S,6S)-methyl 4-hydroxy-6-((E)-3-methoxy-3-oxoprop-1-en-1-yl)-3,5-dimethyltetrahydro-2H-pyran-2-carboxylate (2S,4aR,6R,7S,7aR,8R)-7,8-dimethyltetrahydro-2,6-methanofuro[2,3-b][1,4]dioxin-3(2H)-one (114 mg, 0.62 mmol) was dissolved in a mixture of methanol (1 mL) and tetrahydrofuran (0.2 mL), cooled to 0° C. and treated with trimethyl phosphonoacetate (0.15 mL, 1.5 equiv). Sodium methoxide (25% in methanol, 0.169 mL, 3.0 equiv) was added over 5 min and the resulting mixture was stirred at 0° C. for 40 min. The mixture was diluted with 2-methoxy-2-methylpropane (10 mL), and washed twice with water (5 mL) and then with sat. NH4Cl (5 mL) and brine (5 mL). The organic layer was concentrated in vacuo to give the title compound (117 mg, 70%) as a white solid. $^1$H NMR (CDCl$_3$, 400 MHz): δ 6.90 (dd, 1H), 6.38 (dd, 1H), 4.19 (m, 2H), 4.12 (m, 1H), 3.82 (s, 31H), 3.78 (s, 3H), 2.40 (m, 1H), 2.12 (m, 1H), 1.76 (bd, 1H), 0.98 (d, 3H), 0.98 (d, 3H).

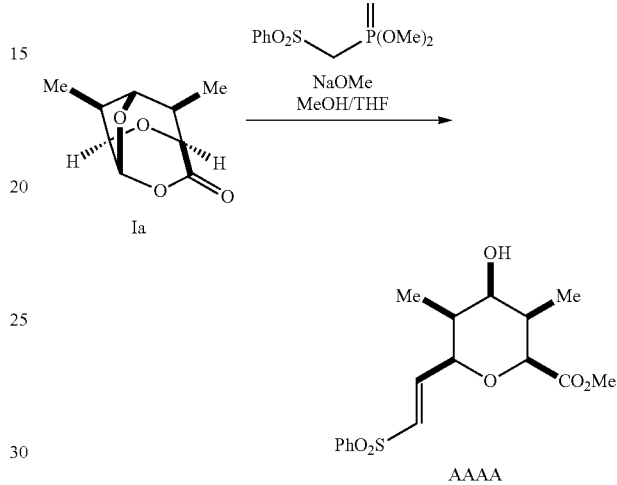

(2S,3R,4R,5S,6R)-methyl 4-hydroxy-3,5-dimethyl-6-((E)-2-(phenysulfonyl) vinyl)tetrahydro-2H-pyran-2-carboxylate A mixture of (2S,4aR,6R,7S,7aR,8R)-7,8-dimethyltetrahydro-2,6-methanofuro[2,3-b][1,4]dioxin-3(2H)-one (5.25 g, 28.5 mmol) and dimethyl ((phenylsulfonyl)methyl)phosphonate (8.75 g, 30.0 mmol, 1.05 equiv) was dissolved in a mixture of methanol (54.6 mL) and tetrahydrofuran (27.3 mL). After cooling to 0° C., the mixture was treated with sodium methoxide (25% solution in methanol, 5.97 mL, 2.3 equiv) and stirred at 0° C. for 1 h.

The mixture was diluted with 2-methoxy-2-methylpropane (100 mL) and sequentially washed with water (50 mL) and saturated aqueous NaHCO3 (50 mL). The aqueous layers were combined and back-extracted with 2-methoxy-2-methylpropane (50 mL). The organic layers were combined, dried over MgSO4 and concentrated in vacuo to give the title compound (10.3 g, 97%). $^1$H NMR (CDCl$_3$, 400 MHz): δ 7.92 (m, 2H), 7.62 (m, 1H), 7.58 (m, 2H), 6.90 (dd, 1H), 6.82 (dd, 1H), 4.22 (m, 1H), 4.19 (m, 1H), 4.13 (d, 1H), 4.10 (t, 1H), 3.78 (s, 3H), 2.36 (m, 1H), 2.15 (m, 1H), 0.91 (d, 3H), 0.88 (d, 3H).

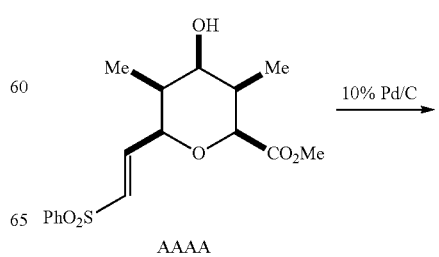

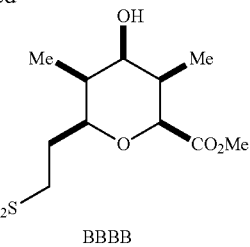

BBBB (2S,3R,4R,5S,6S)-methyl 4-hydroxy-3,5-dimethyl-6-(2-(phenylsulfonyl)ethyl)tetrahydro-2H-pyran-2-carboxylate (2S,3R,4R,5S,6R)-methyl 4-hydroxy-3,5-dimethyl-6-((E)-2-(phenylsulfonyl)vinyl)tetrahydro-2H-pyran-2-carboxylate (9.1 g, 25.7 mmol) was dissolved in a mixture of ethyl acetate (100 mL) and methanol (20 mL), and treated with 10% Pd/C (50% wet, Degussa type E101 NE/W, 550 mg). The mixture was stirred under hydrogen atmosphere (balloon) for 15 h. The catalyst was filtered off using celite pad and washed with ethyl acetate. The filtrate was concentrated in vacuo to give the title compound (11.23 g), which was used for the next step without further purification. $^1$H NMR (CDCl$_3$, 400 MHz): δ 7.96 (m, 2H), 7.65 (m, 1H), 7.61 (m, 2H), 4.20 (m, 1H), 4.00 (m, 1H), 3.78 (s, 3H), 3.52 (m, 1H), 3.38 (m, 1H), 3.22 (m, 1H), 2.22 (m, 1H), 2.18 (m, 1H), 1.92 (m, 2H), 0.94 (d, 3H), 0.90 (d, 3H).

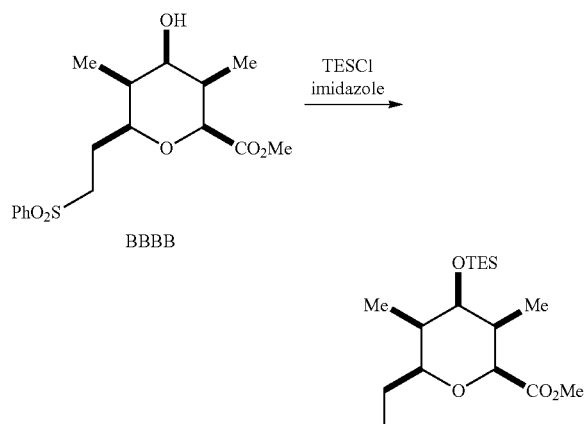

(2S,3S,4R,5R,6S)-methyl 3,5-dimethyl-6-(2-(phenylsulfonyl)ethyl)-4-((triethylsilyl) oxy)tetrahydro-2H-pyran-2-carboxylate A solution of (2S,3R,4R,5S,6S)-methyl 4-hydroxy-3,5-dimethyl-6-(2-(phenylsulfonyl)ethyl)tetrahydro-2H-pyran-2-carboxylate (9.15 g, 25.7 mmol) in methylene chloride (100 mL) was cooled to 0° C. and treated with imidazole (3.5 g, 2.0 equiv) and chlorotriethylsilane (4.74 mL, 1.1 equiv). The mixture was stirred at rt for 21 h. The resulting mixture was diluted with 2-methoxy-2-methylpropane (150 mL), sequentially washed with water (70 mL) and brine (30 mL), and concentrated in vacuo. The resulting crude product was purified by column chromatography (ethyl acetate/n-heptane=1/10 to 1/3) to give the title compound (10.75 g, 94% for two steps). $^1$H NMR (CDCl$_3$, 400 MHz): δ 7.96 (m, 2H), 7.65 (m, 1H), 7.61 (m, 2H), 3.98 (m, 1H), 3.90 (t, 1H), 3.78 (s, 3H), 3.49 (m, 1H), 3.38 (m, 1H), 3.21 (m, 1H), 2.16 (m, 2H), 1.92 (m, 1H), 1.78 (m, 1H), 1.00 (t, 9H), 0.92 (d, 3H), 0.88 (d, 3H), 0.62 (q, 6H).

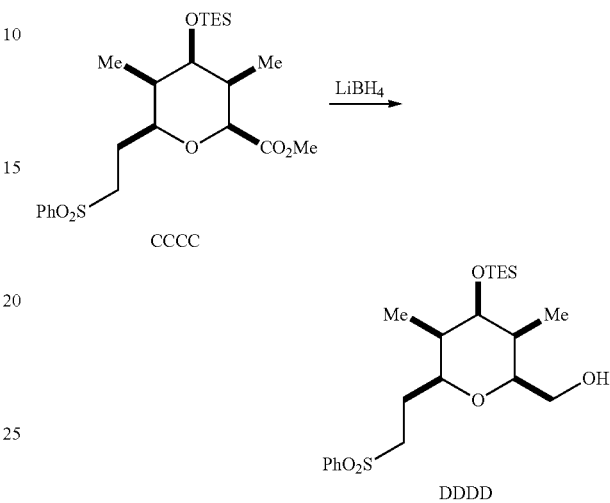

((2S,3S,4R,5R,6S)-3,5-dimethyl-6-(2-(phenylsulfonyl)ethyl)-4-((triethylsilyl)oxy)tetrahydro-2H-pyran-2-yl)methanol (2S,3S,4R,5R,6S)-methyl 3,5-dimethyl-6-(2-(phenylsulfonyl)ethyl)-4-((triethylsilyl)oxy)tetrahydro-2H-pyran-2-carboxylate (1.0 g, 2.1 mmol) was dissolved in tetrahydrofuran (13 mL) and cooled to 0° C. 2 M Lithium tetrahydroborate in tetrahydrofuran (2.46 mL, 2.3 equiv) was added and the resulting mixture was stirred at rt for 22 h. After cooing to 0° C., the mixture was diluted with 2-methoxy-2-methylpropane (20 mL) and treated with 20 wt % citric acid (3.87 mL) maintaining the internal temperature below 10° C. The mixture was vigorously stirred for 10 min. The organic layer was separated and the aqueous layer was extracted with 2-methoxy-2-methylpropane (20 mL). The organic layers were combined, washed twice with sat. NaHCO3 and then concentrated under vacuum to give the title compound (0.90 g, 95%) as a clear oil. $^1$H NMR (CDCl$_3$, 400 MHz): δ 7.95 (m, 2H), 7.65 (m, 1H), 7.60 (m, 2H), 3.83 (m, 1H), 3.72 (m, 1H), 3.40-3.52 (m, 3H), 3.32 (m, 1H), 3.19 (m, 1H), 2.10 (m, 1H), 1.70-1.90 (m, 3H), 0.80-1.00 (m, 15H), 0.60 (q, 6H).

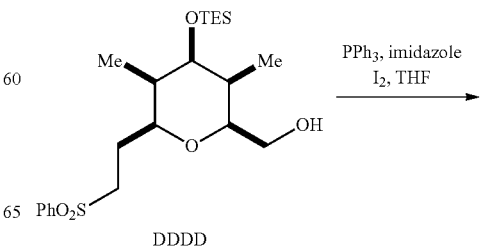

DDDD

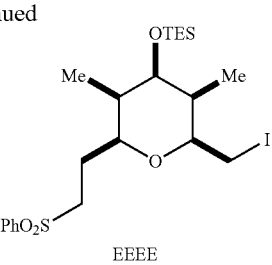

EEEE

Triethyl(((2S,3S,4R,5R,6S)-2-(iodomethyl)-3,5-dimethyl-6-(2-(phenylsulfonyl)ethyl)tetrahydro-2H-pyran-4-yl)oxy)silane ((2S,3S,4R,5R,6S)-3,5-dimethyl-6-(2-(phenylsulfonyl) ethyl)-4-((triethylsilyl)oxy)tetrahydro-2H-pyran-2-yl) methanol (0.18 g, 0.40 mmol) was dissolved in tetrahydrofuran (3 mL) and treated with triphenylphosphine (0.21 g, 2.0 equiv) and imidazole (82 mg, 3.0 equiv). After cooling to 0° C., the mixture was treated with iodine (0.15 g, 2.0 equiv) and stirred at rt for 5 h. More triphenylphosphine (0.21 g, 2.0 equiv), imidazole (82 mg, 3.0 equiv) and iodine (0.15 g, 2.0 equiv) were added, and stirring was continued at rt for 15 h and at 40° C. for 5 h. After cooling to rt, the reaction was quenched with 10% aqueous sodium thiosulfate solution (5 mL) and extracted with MTBE. After concentration, the crude product was purified by column chromatography (MTBE/n-heptane=1/10 to 1/3) to give the title compound (172 mg, 77%). $^1$H NMR (CDCl$_3$, 400 MHz): δ 7.95 (m, 2H), 7.65 (m, 1H), 7.60 (m, 2H), 3.80 (m, 1H), 3.42-3.58 (m, 2H), 3.40 (m, 1H), 3.24 (m, 1H), 3.22 (m, 1H), 2.10 (m, 1H), 1.98 (m, 1H), 1.82 (m, 1H), 1.68 (m, 1H), 0.98 (t, 9H), 0.86 (d, 3H), 0.82 (d, 3H), 0.60 (q, 6H).

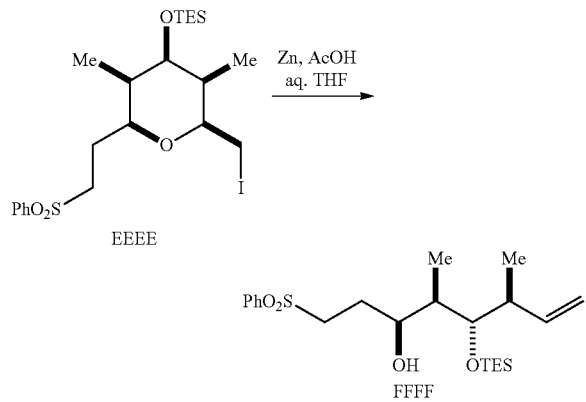

(3S,4R,5S,6S)-4,6-dimethyl-1-(phenylsulfonyl)-5-((triethylsilyl)oxy)oct-7-en-3-ol To a cooled (0° C.) mixture of zinc (0.101 g, 5 equiv) and acetic acid (0.035 mL, 2.0 equiv) in water (0.3 mL) was added a solution of triethyl(((2S,3S,4R,5R,6S)-2-(iodomethyl)-3,5-dimethyl-6-(2-(phenylsulfonyl)ethyl)tetrahydro-2H-pyran-4-yl)oxy)silane (0.17 g, 1.3 mmol) in tetrahydrofuran (1 mL). After stirring at 0° C. for 2 h, the mixture was diluted with 2-methoxy-2-methylpropane (20 mL). The mixture was sequentially washed with water (5 mL) and saturated aqueous NaHCO3 (5 mL), concentrated in vacuo and purified by column chromatography (MTBE/n-heptane=1/10 to 1/2) to give the title compound (104 mg, 79%). $^1$H NMR (CDCl$_3$, 400 MHz): δ 7.93 (m, 2H), 7.63 (m, 1H), 7.58 (m, 2H), 5.74 (m, 1H), 5.02 (m, 2H), 4.01 (m, 1H), 3.55 (dd, 1H), 3.50 (s, 1H), 3.34 (m, 1H), 3.08 (m, 1H), 2.39 (m, 1H), 1.88 (m, 1H), 1.60-1.76 (m, 2H), 0.86-0.96 (m, 15H), 0.60 (m, 6H).

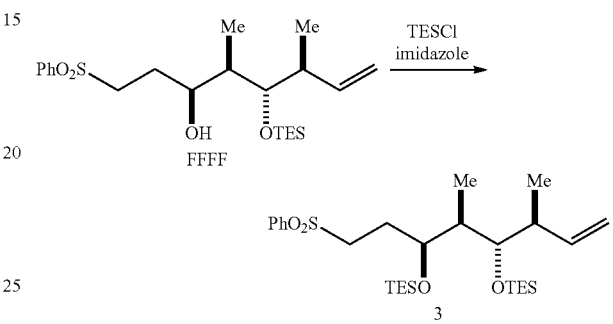

(5S,6R,7S)-5-((S)-but-3-en-2-yl)-3,3,9,9-tetraethyl-6-methyl-7-(2-(phenylsulfonyl)ethyl)-4,8-dioxa-3,9-disilaundecane A solution of (3S,4R,5S,6S)-4,6-dimethyl-1-(phenylsulfonyl)-5-((triethylsilyl)oxy)oct-7-en-3-ol (0.36 g, 0.84 mmol) in methylene chloride (4.5 mL) was cooled to 0° C., treated with imidazole (0.172 g, 3.0 equiv) and chlorotriethylsilane (0.212 mL, 0.15 equiv), and stirred at rt for 7 h. More imidazole (30 mg, 0.52 equiv) and chlorotriethylsilane (20 □L, 0.14 equiv) were added and stirring was continued at rt for additional 16 h. After quenching the reaction with water (10 mL), the mixture was extracted with 2-methoxy-2-methylpropane (10 mL). The separated organic layer was washed with brine and concentrated in vacuo. The crude product was purified by column chromatography (MTBE/n-heptane=1/20 to 1/5) to give the title compound (342 mg, 75%). $^1$H NMR (CDCl$_3$, 400 MHz): δ 7.95 (m, 2H), 7.66 (m, 1H), 7.61 (m, 2H), 5.87 (m, 1H), 4.95 (m, 2H), 3.82 (m, 1H), 3.49 (dd, 1H), 3.20 (m, 1H), 3.06 (m, 1H), 2.26 (m, 1H), 1.8-2.0 (m, 2H), 1.50 (m, 1H), 0.86-1.00 (min, 21H), 0.82 (d, 3H), 0.50-0.66 (m, 12H).

E. Synthesis of Protected Pentads 4 and 5

Protected pentads of Formulas 4 and 5 were synthesized from a compound of Formula Ia as shown in Scheme 4 and described below.

Scheme 4

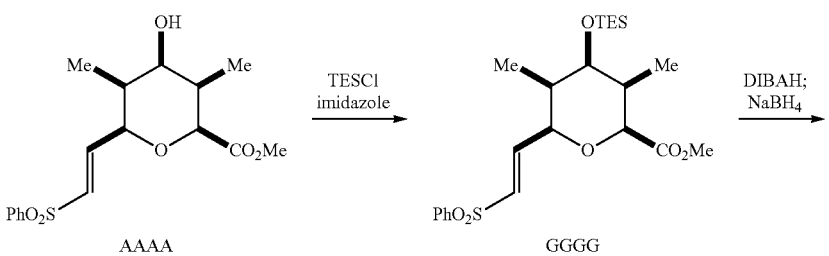

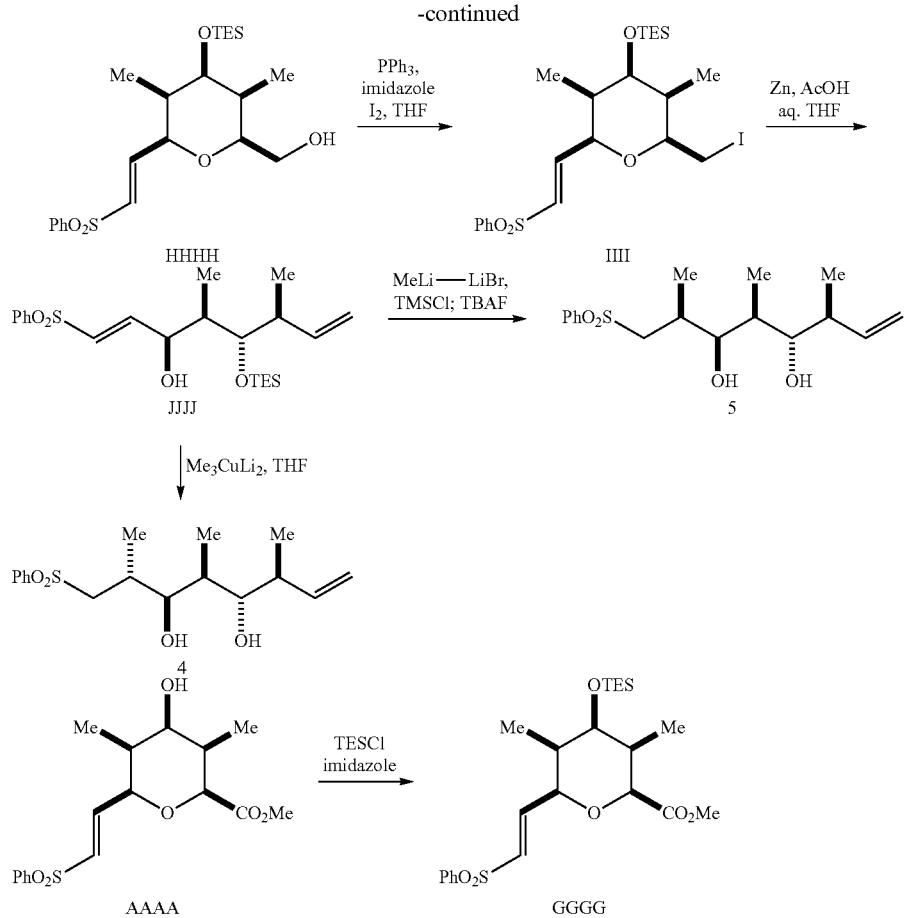

(2S,3S,4R,5R,6R)-methyl 3,5-dimethyl-6-((E)-2-(phenylsulfonyl)vinyl)-4-((triethylsilyl)oxy)tetrahydro-2H-pyran-2-carboxylate A solution of (2S,3R,4R,5S,6R)-methyl 4-hydroxy-3,5-dimethyl-6-((E)-2-(phenylsulfonyl)vinyl)tetrahydro-2H-pyran-2-carboxylate (1.0 g, 2.8 mmol) in methylene chloride was cooled to 0° C. and treated with imidazole (0.406 g, 2.1 equiv) and chlorotriethylsilane (0.521 mL, 1.1 equiv). After stirring at rt for 4 h, the mixture was diluted with 2-methoxy-2-methylpropane (20 mL) and washed with water (10 mL) and brine (10 mL). After concentration, the crude product was purified by column chromatography (MTBE/n-heptane=1/10 to 1/2) to give the title compound (1.11 g, 88%). $^1$H NMR (CDCl$_3$, 400 MHz): δ 7.92 (m, 2H), 7.65 (m, 1H), 7.58 (m, 2H), 6.90 (dd, 1H), 6.80 (dd, 1H), 4.20 (m, 1H), 4.12 (m, 1H), 4.02 (t, 1H), 3.78 (s, 3H), 2.22 (m, 1H), 2.02 (m, 1H), 1.01 (t, 9H), 0.89 (d, 3H), 0.87 (d, 3H), 0.64 (q, 6H).

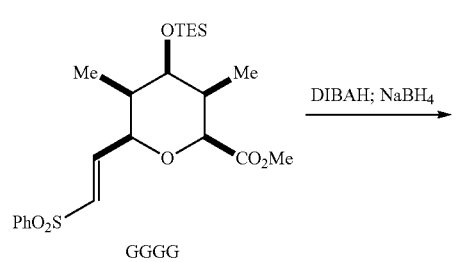

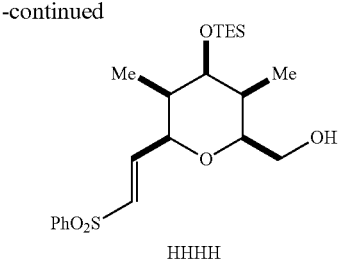

((2S,3S,4R,5R,6R)-3,5-dimethyl-6-((E)-2-(phenylsulfonyl)vinyl)-4-((triethylsilyl)oxy)tetrahydro-2H-pyran-2-yl)methanol To a cooled (−70° C.) solution of (2S3S,4R,5R,6R)-methyl 3,5-dimethyl-6-((E)-2-(phenylsulfonyl)vinyl)-4-((triethylsilyl)oxy)tetrahydro-2H-pyran-2-carboxylate (7.91 g, 16.9 mmol) in methylene chloride (80 mL) was added 1 M diisobutylaluminum hydride in toluene (37.1 mL, 2.2 equiv). After stirring at −65° C. for 1 h, additional 1 M diisobutylaluminum hydride in toluene (5.1 mL, 0.3 equiv) was added and stirring was continued at −65° C. for additional 0.5 h. After quenching the reaction with methanol (3.3 mL), the mixture was stirred at −65° C. for 5 min, poured into saturated aqueous sodium potassium tartrate (180 mL), and vigorously stirred at rt for 1 h. Then, the mixture was extracted twice with 2-methoxy-2-methylpropane (100 mL). The organic layers were combined and concentrated in vacuo.

The residue was dissolved in methanol (66 mL), cooled to 0° C., and treated with sodium tetrahydroborate (0.19 g, 0.3 equiv). After stirring for 1 h at 0° C., the reaction was quenched with 0.1 M hydrogen chloride in water (66 mL) and the mixture was extracted twice with 2-methoxy-2-methylpropane (60 mL). The organic layers were combined, sequentially washed with sat. NaHCO3 (30 mL) and brine (30 mL), and concentrated in vacuo. The crude product was purified by column chromatography (ethyl acetate/n-heptane=1/10 to 1/2) to give the title compound (4.76 g, 95%). $^1$H NMR (CDCl$_3$, 400 MHz): δ 7.93 (m, 2H), 7.66 (m, 1H), 7.57 (m, 2H), 6.90 (dd, 1H), 6.64 (dd, 1H), 4.22 (m, 1H), 3.95 (t, 1H), 3.78 (m, 1H), 3.58 (m, 1H), 3.52 (m, 1H), 2.00 (m, 1H), 1.82 (m, 1H), 1.79 (m, 1H), 0.98 (t, 9H), 0.86 (d, 3H), 0.82 (d, 3H), 0.62 (q, 6H).

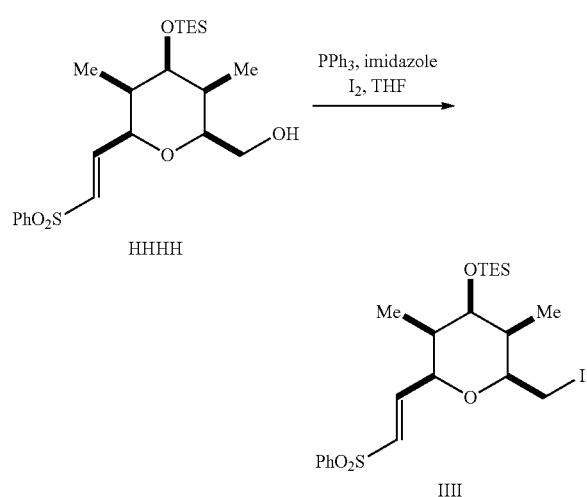

triethyl((2S,3S,4R,5R,6R)-2-(iodomethyl)-3,5-dimethyl-6-((E)-2-(phenylsulfonyl)vinyl)tetrahydro-2H-pyran-4-yl)oxy)silane ((2S,3S,4R,5R,6R)-3,5-dimethyl-6-((E)-2-(phenylsulfonyl)vinyl)-4-((triethylsilyl)oxy)tetrahydro-2H-pyran-2-yl)methanol (4.54 g, 10.3 mmol) was dissolved in tetrahydrofuran (85 mL) and treated with triphenylphosphine (9.47 g, 3.5 equiv) and imidazole (4.21 g, 6 equiv). After addition of iodine (7.85 g, 3 equiv), the mixture was stirred at rt for 1 h and at 40° C. for 22 h. The mixture was cooled to rt and diluted with n-heptane (50 mL). The resulting precipitate was filtered and washed with 2-methoxy-2-methylpropane (100 mL). The filtrate was sequentially washed with 10% aqueous sodium thiosulfate solution (80 mL) and brine (30 mL), and concentrated in vacuo. The crude product was purified by column chromatography (MTBE/heptane=1/10 to 1/5) to give the title compound (4.72 g, 83%). $^1$H NMR (CDCl$_3$, 400 MHz): δ 7.93 (m, 2H), 7.66 (m, 1H), 7.57 (m, 2H), 6.87 (dd, 1H), 6.71 (dd, 1H), 4.19 (m, 1H), 3.93 (t, 1H), 3.63 (m, 1H), 3.28 (dd, 1H), 3.10 (dd, 1H), 2.10 (m, 1H), 1.94 (m, 1H), 1.00 (t, 9H), 0.86 (d, 3H), 0.81 (d, 3H), 0.64 (q, 6H).

(3R,4R,5S,6S,E)-4,6-dimethyl-1-(phenylsulfonyl)-5-((triethylsilyl)oxy)octa-1,7-dien-3-ol To a cooled (0° C.) mixture of zinc (100 mesh, 2.8 g, 5.0 equiv), lead dichloride (0.24 g) and acetic acid (0.975 mL, 2 equiv) in water (8.4 mL) was added a solution of triethyl (((2S,3S,4R,5R,6R)-2-(iodomethyl)-3,5-dimethyl-6-((E)-2-(phenylsulfonyl)vinyl)tetrahydro-2H-pyran-4-yl)oxy)silane (4.72 g, 8.6 mmol) in tetrahydrofuran (43.7 mL). After stirring at 0° C. for 2 h, additional zinc (1 g, 1.8 equiv) was added and stirring was continued at 0° C. for 3 h and at rt for 12 h. Additional zinc (powder, 1.4 g, 2.5 equiv) and acetic acid (0.15 mL, 0.3 equiv) were added and stirring was continued at rt for another 7 h. After removal of unreacted zinc by filtration, the filtrate was washed with saturated aqueous NaHCO3 (17 mL), and the aqueous layer was back-extracted with 2-methoxy-2-methylpropane (50 mL). The organic layers were combined, washed with brine, and concentrated in vacuo. The crude product was purified by column chromatography (MTBE/n-heptane=1/10 to 1/2) to give the title compound (2.6 g, 71%). $^1$H NMR (CDCl$_3$, 400 MHz): δ 7.92 (m, 2H), 7.63 (m, 1H), 7.55 (m, 2H), 6.90 (dd, ii), 6.68 (dd, 1H), 5.80 (m, 1H), 5.10 (m, 2H), 4.88 (4.19 (m, 1H), 3.80 (s, 1H), 3.70 (m, 1H), 2.50 (m, 1H), 1.92 (m, 1H), 1.08 (d, 3H), 0.98 (t, 9H), 0.91 (d, 3H), 0.66 (q, 6H).

(2S,3R,4R,5S,6S)-2,4,6-trimethyl-1-(phenylsulfonyl)oct-7-ene-3,5-diol (3R,4R,5S,6S,E)-4,6-dimethyl-1-(phenylsulfonyl)-5-((triethylsilyl)oxy)octa-1,7-dien-3-ol (51 mg, 0.12 mmol) in tetrahydrofuran (2 mL) was cooled to −78° C. and treated with 1.5 M methyllithium-lithium bromide complex in ether (0.24 mL, 3.0 equiv). After stirring at −78 C∼−60° C. for 1 h, the mixture was treated with chlorotrimethylsilane (46 μL, 3.0 equiv) and stirred at −60° C. for additional 20 min. After cooling back to −78° C., the mixture was treated with 1.5 M methyllithium-lithium bromide complex in ether (0.24 mL, 3.0 equiv) and warmed up to −40° C. over 3 h. The reaction was quenched with sat.NH4Cl and extracted with MTBE. The organic layer was dried over MgSO4 and concentrated in vacuo.

The residue was dissolved in tetrahydrofuran (2 mL), treated with 1 M tetra-n-butylammonium fluoride in tetrahydrofuran (0.36 mL), and stirred at rt for 1 h. After dilution with MTBE, the mixture was washed with water and dried over MgSO4. The crude product was purified by column chromatography (ethyl acetate/n-heptane=1/10 to 2/1) to give the title compound (7 mg, 20%). $^1$H NMR (CDCl$_3$, 400 MHz): δ 7.95 (m, 2H), 7.70 (m, 1H), 7.61 (m, 2H), 5.70 (m, 1H), 5.20 (m, 2H), 3.83 (dd, 1H), 3.32 (m, 1H), 3.28 (dd, 1H), 3.23 (ds, 1H), 2.93 (dd, 1H), 2.40 (m, 1H), 2.26 (m, 1H), 2.20 (bs, 1H), 1.70 (m, 1H), 1.19 (d, 3H), 1.02 (d, 3H), 0.94 (d, 3H).

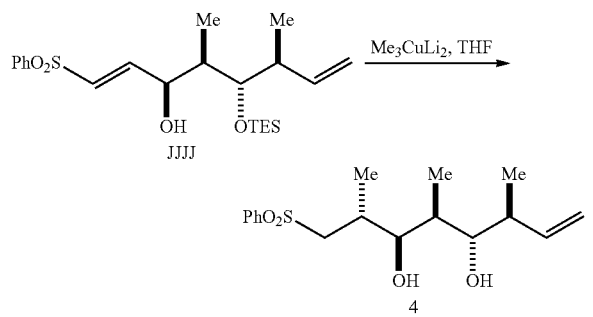

(2R,3R,4R,5S,6S)-2,4,6-trimethyl-1-(phenylsulfonyl)oct-7-ene-3,5-diol

To a cold (0° C.) suspension of copper(I) iodide (0.45 g, 5 equiv) in tetrahydrofuran (10 mL) was added 1.6 M methyllithium in ether (4.42 mL, 15 equiv). After stirring at 0° C. for 30 min, the mixture was treated with a solution of (3R,4R,5S,6S,E)-4,6-dimethyl-1-(phenylsulfonyl)-5-((triethylsilyl)oxy)octa-1,7-dien-3-ol (0.2 g, 0.47 mmol) in tetrahydrofuran (2 mL and 1 mL for rinse). The mixture was stirred at 0° C. for 1 h and at rt for 1 h. The reaction was quenched with a mixture of 28% ammonium hydroxide (4 mL) and saturated NH4Cl (40 mL), and the resulting mixture was extracted with MTBE. The organic layer was washed with brine and concentrated in vacuo. The crude product was purified by column chromatography (ethyl acetate/n-heptane=1/10 to 1/2) to give the title compound (95 mg, 62%). $^1$H NMR (CDCl$_3$, 400 MHz): δ 7.95 (m, 2H), 7.66 (m, 1H), 7.60 (m, 2H), 5.70 (m, 1H), 5.20 (m, 2H), 3.50-3.70 (m, 2H), 3.37 (m, 1H), 2.90 (dd, 1H), 2.40 (m, 1H), 2.28 (m, 1H), 1.90 (m, 1H), 1.15 (d, 3H), 1.01 (2d, 6H).

F. Exemplary Elaboration of Protected Tetrad of Formula 3

The protected tetrad of Formula 3 was used to prepare intermediates of aplyronine as described below.

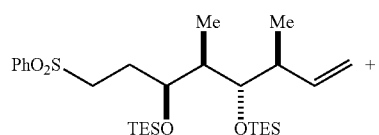

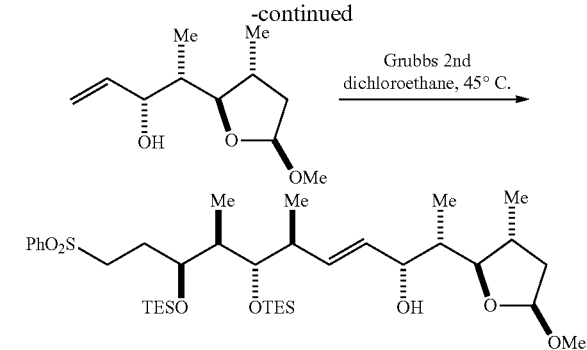

(2S,3R,6S,7S,8R,9S,E)-2-((2R,3R,5S)-5-methoxy-3-methyltetrahydrofuran-2-yl)-6,8-dimethyl-11-(phenylsulfonyl)-7,9-bis((triethylsilyl)oxy)undec-4-en-3-ol A mixture of (5S,6R,7S)-5-((S)-but-3-en-2-yl)-3,3,9,9-tetraethyl-6-methyl-7-(2-(phenylsulfonyl)ethyl)-4,8-dioxa-3,9-disilaundecane (84 mg, 0.16 mmol) and (3R,4S)-4-((2R,3R,5S)-5-methoxy-3-methyltetrahydrofuran-2-yl)pent-1-en-3-ol (21 mg, 0.11 mmol) was dissolved in a degassed 1,2-dichloroethane (3 mL) and heated to 45° C. After stirring at 45° C. for 5 min, the mixture was treated with Grubbs 2$^{nd}$ generation catalyst (6 mg, 7 μmol) and stirred at 45° C. for 21 h and at 60° C. for 2 h. The mixture was cooled to rt and concentrated in vacuo. The residue was purified by column chromatography (ethyl acetate/n-heptane=1/10 to 2/1) to give the title compound (8 mg, 10%) along with 67% of recovered starting material. $^1$H NMR (CDCl$_3$, 400 MHz): δ 7.95 (m, 2H), 7.70 (m, 1H), 7.61 (m, 2H), 5.76 (dd, 1H), 5.49 (dd, 1H), 4.98 (d, 1H), 4.31 (M, 1H), 3.83 (bq, 1H), 3.59 (dd, 1H), 3.52 (dd, 1H), 3.38 (s, 3H), 3.16 (m, 1H), 3.13 (d, 1H), 3.05 (m, 1H), 2.32 (m, 2H), 2.13 (m, 1H), 1.90 (m, 2H), 1.83 (m, 1H), 1.65 (m, 1H), 1.49 (m, 1H), 1.12 (d, 3H), 0.9-1.4 (m, 24H), 0.81 (d, 3H), 0.62 (q, 6H), 0.56 (q, 6H).

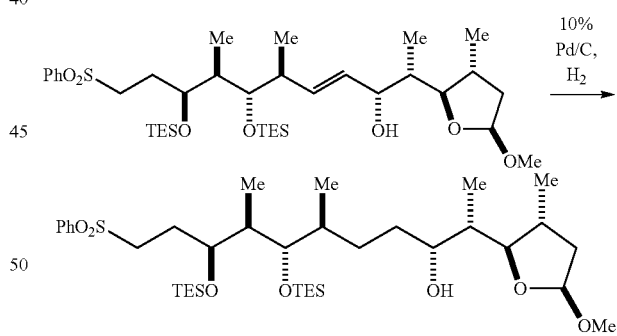

(2S,3R,6S,7S,8R,9S)-2-((2R,3R,5S)-5-methoxy-3-methyltetrahydrofuran-2-yl)-6,8-dimethyl-11-(phenylsulfonyl)-7,9-bis((triethylsilyl)oxy)undecan-3-ol (2S,3R,6S,7S,8R,9S,E)-2-((2R,3R,5S)-5-methoxy-3-methyltetrahydrofuran-2-yl)-6,8-dimethyl-11-(phenylsulfonyl)-7,9-bis((triethylsilyl)oxy)undec-4-en-3-ol (8 mg, 11 μmol) was dissolved in ethyl acetate (3 mL) and treated with 10% Pd on C (5 mg). The mixture was stirred at rt under hydrogen atmosphere (balloon) for 1 h. The catalyst was filtered off and rinsed with ethyl acetate. The filtrate was concentrated in vacuo to give the title compound in quantatative yield. $^1$H NMR (CDCl$_3$, 400 MHz): δ 7.95 (m, 2H), 7.69 (m, 1H), 7.61 (m, 2H), 4.95 (d, 1H), 3.84 (m, 2H), 3.60 (dd, 1H), 3.45 (m, 1H), 3.37 (s, 3H), 3.35 (d, 1H), 3.03-3.22 (m, 2H), 2.31 (m, 1H), 2.14 (m, 1H), 1.91 (m, 2H), 1.59-1.75 (m, 3H), 1.45-1.55 (m, 4H), 1.35 (m, 1H), 1.09 (d, 3H), 0.85-1.00 (m, 24H), 0.81 (d, 3H), 0.50-0.63 (m, 12H).

We claim:

1. A process for preparing a compound of Formula 1:

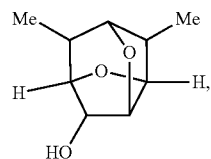

comprising the steps of:
reacting 6,8-dimethyl-3,9-dioxatricyclo[3.3.1.0²,⁴]nonan-7-one with a reducing agent to form an intermediate having the following structure:

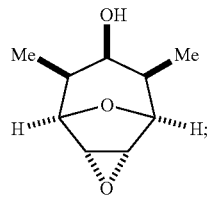

and
reacting the intermediate with an acid to form the compound of Formula 1.

2. A process for resolving enantiomers of a compound of Formula 1:

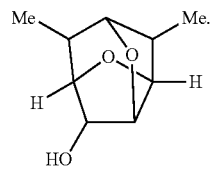

comprising the steps of:
reacting the racemic compound of Formula 1 with phthalic anhydride to form a racemic mixture of phthalates of Formulas 2A and 2B having the structure:

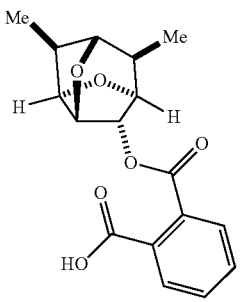

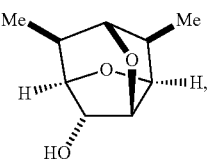

reacting the racemic mixture of phthalates of Formulas 2A and 2B with a first chiral amine in a solvent to form a pair of diastereomeric salts thereof in a solution;
precipitating a first diastereomeric salt of the pair of diastereomeric salts from the solution to provide an isolated first diastereomeric salt and an second diastereomeric salt; and
forming the enantiomers of the compound of Formula 1 from the isolated first diastereomeric salt and the second diastereomeric salt, thereby resolving the enantiomers of the compound of Formula 1".

3. The process of claim 2, wherein the isolated first diastereomeric salt is treated with a base to form a first enantiomeric compound of Formula 1.

4. The process of claim 3, wherein the first enantiomeric compound of Formula 1 is the compound of Formula 1B:

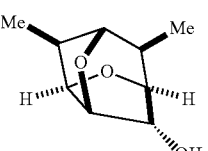

or a salt thereof.

5. The process of claim 2, further comprising the steps of:
acidifying the second diastereomeric salt to form a free phthalate;
reacting the free phthalate with a second chiral amine to reform the second diastereomeric salt in a solution;
precipitating the second diastereomeric salt from the solution to form an isolated second diastereomeric salt; and
forming a second enantiomeric compound of Formula 1 from the isolated second diastereomeric salt.

6. The process of claim 5, wherein the second enantiomeric compound of Formula 1 is the compound of Formula 1A

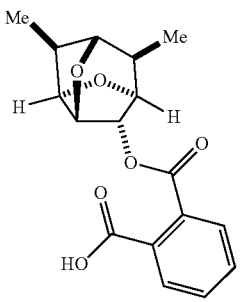

* * * * *